US009295826B2

(12) United States Patent
Bertrand et al.

(10) Patent No.: US 9,295,826 B2
(45) Date of Patent: Mar. 29, 2016

(54) FLUID FLOW CONTROL DEVICES, ROTORS AND MAGNETS WITH INCREASED RESISTANCE TO INADVERTENT SETTING CHANGE AND IMPROVED ACCESSORY TOOL COUPLING

(71) Applicant: MEDTRONIC XOMED, INC, Jacksonville, FL (US)

(72) Inventors: W. Jeff Bertrand, Ventura, CA (US); Lori Speckman, Ventura, CA (US); Manfred Karl Luedi, Jacksonville, FL (US); Chun Man Alan Leung, Jacksonville, FL (US); Lawrence Hampton, Santa Maria, CA (US); Deep Shah, Santa Barbara, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 329 days.

(21) Appl. No.: 13/804,875

(22) Filed: Mar. 14, 2013

(65) Prior Publication Data
US 2013/0345646 A1    Dec. 26, 2013

Related U.S. Application Data

(60) Provisional application No. 61/662,664, filed on Jun. 21, 2012.

(51) Int. Cl.
*A61M 39/22*    (2006.01)
*F16K 31/08*    (2006.01)
*A61M 27/00*    (2006.01)

(52) U.S. Cl.
CPC ............. *A61M 39/22* (2013.01); *A61M 27/006* (2013.01); *F16K 31/088* (2013.01)

(58) Field of Classification Search
CPC ................ A61M 39/22; A61M 39/24; A61M 2039/226; A61M 2039/248; A61M 27/006; F16K 31/08; F16K 31/084; F16K 35/16
See application file for complete search history.

(56) References Cited

U.S. PATENT DOCUMENTS

| 5,637,083 | A | * | 6/1997 | Bertrand et al. | 604/9 |
|---|---|---|---|---|---|
| 5,643,194 | A | * | 7/1997 | Negre | 604/8 |
| 5,758,667 | A | | 6/1998 | Slettenmark | |
| 5,944,023 | A | | 8/1999 | Johnson et al. | |
| 6,050,969 | A | | 4/2000 | Kraus | |
| 6,138,681 | A | | 10/2000 | Chen et al. | |
| 6,234,956 | B1 | | 5/2001 | He et al. | |
| 6,391,019 | B1 | | 5/2002 | Ito | |
| 6,417,750 | B1 | | 7/2002 | Sohn | |
| 6,439,538 | B1 | | 8/2002 | Ito | |

(Continued)

FOREIGN PATENT DOCUMENTS

| DE | 102007059300 | 6/2009 |
|---|---|---|
| WO | 2009066133 | 5/2009 |
| WO | 2011136241 | 3/2011 |

*Primary Examiner* — Andrew Gilbert
(74) *Attorney, Agent, or Firm* — Dicke, Billig & Czaja, PLLC

(57) ABSTRACT

Implantable physiological shunt systems and related fluid flow control devices and accessories for use therewith. Devices, systems and methods relating to implantable medical fluid flow control devices, rotors and magnets with increased resistance to inadvertent setting changes. Devices, systems and methods relating implantable medical fluid flow control devices, rotors and magnets which provide improved magnetic coupling to fluid flow control device accessories such as adjustment tools.

3 Claims, 15 Drawing Sheets

(56) References Cited

U.S. PATENT DOCUMENTS

| | | |
|---|---|---|
| 6,657,351 B2 | 12/2003 | Chen et al. |
| 6,702,249 B2 | 3/2004 | Ito |
| 6,840,917 B2 | 1/2005 | Marion |
| 6,951,059 B2 | 10/2005 | Moskowitz et al. |
| 7,057,369 B2 | 6/2006 | Hoffmann |
| 7,255,682 B1 | 8/2007 | Bartol, Jr. et al. |
| 7,334,594 B2 | 2/2008 | Ludin |
| 7,338,028 B2 | 3/2008 | Zimmerling et al. |
| 7,422,566 B2 | 9/2008 | Miethke |
| 7,485,105 B2 | 2/2009 | Wolf |
| 7,771,381 B2 | 8/2010 | McCusker et al. |
| 7,856,987 B2 | 12/2010 | Bertrand et al. |
| 7,921,571 B2 | 4/2011 | Moureaux et al. |
| 8,038,641 B2 | 10/2011 | Soares et al. |
| 8,057,422 B2 | 11/2011 | Wolf, II |
| 8,123,714 B2 | 2/2012 | Ludin et al. |
| 8,171,938 B2 | 5/2012 | Bengtson |
| 8,241,240 B2 | 8/2012 | Murphy |
| 8,322,365 B2 | 12/2012 | Wilson et al. |
| 8,398,577 B2 | 3/2013 | Burnett |
| 8,398,617 B2 | 3/2013 | Ginggen et al. |
| 8,518,023 B2 | 8/2013 | Roth et al. |
| 8,539,956 B2 | 9/2013 | Bertrand et al. |
| 8,591,499 B2 | 11/2013 | Girardin et al. |
| 8,617,142 B2 | 12/2013 | Wilson et al. |
| 8,622,978 B2 * | 1/2014 | Bertrand et al. .............. 604/248 |
| 8,630,695 B2 | 1/2014 | Negre et al. |
| 8,733,394 B2 | 5/2014 | Negre et al. |
| 8,753,331 B2 | 6/2014 | Murphy |
| 8,763,637 B2 | 7/2014 | Soldo et al. |
| 8,813,757 B2 | 8/2014 | Prisco et al. |
| 2001/0022350 A1 | 9/2001 | Ito |
| 2002/0022793 A1 * | 2/2002 | Bertrand et al. .................. 604/9 |
| 2005/0055009 A1 | 3/2005 | Rosenberg |
| 2005/0092335 A1 * | 5/2005 | Bertrand et al. .............. 128/899 |
| 2005/0096579 A1 * | 5/2005 | Bertrand et al. .................. 604/9 |
| 2007/0004999 A1 | 1/2007 | Miethke |
| 2008/0083413 A1 | 4/2008 | Forsell |
| 2009/0076597 A1 | 3/2009 | Dahlgren et al. |
| 2011/0048539 A1 | 3/2011 | Negre et al. |
| 2011/0066098 A1 | 3/2011 | Stergiopulos |
| 2011/0105991 A1 | 5/2011 | Roth et al. |
| 2011/0105992 A1 | 5/2011 | Girardin et al. |
| 2011/0105993 A1 | 5/2011 | Girardin et al. |
| 2011/0118589 A1 | 5/2011 | Negre et al. |
| 2011/0295104 A1 | 12/2011 | Teitelbaum et al. |
| 2012/0029414 A1 | 2/2012 | Wolf, II |
| 2012/0046595 A1 * | 2/2012 | Wilson et al. .................... 604/9 |
| 2012/0046596 A1 | 2/2012 | Ludin et al. |
| 2012/0197178 A1 | 8/2012 | Prisco et al. |
| 2013/0002243 A1 | 1/2013 | Bertrand et al. |
| 2013/0085441 A1 * | 4/2013 | Aihara .............................. 604/9 |
| 2013/0345646 A1 | 12/2013 | Bertrand et al. |
| 2014/0052047 A1 | 2/2014 | Wilson |
| 2014/0121586 A1 | 5/2014 | Bertrand et al. |
| 2014/0257166 A9 | 9/2014 | Wolf, II |
| 2014/0261793 A1 | 9/2014 | Shah et al. |
| 2014/0276340 A1 | 9/2014 | Ludin et al. |
| 2014/0276346 A1 | 9/2014 | Sadanand |

* cited by examiner

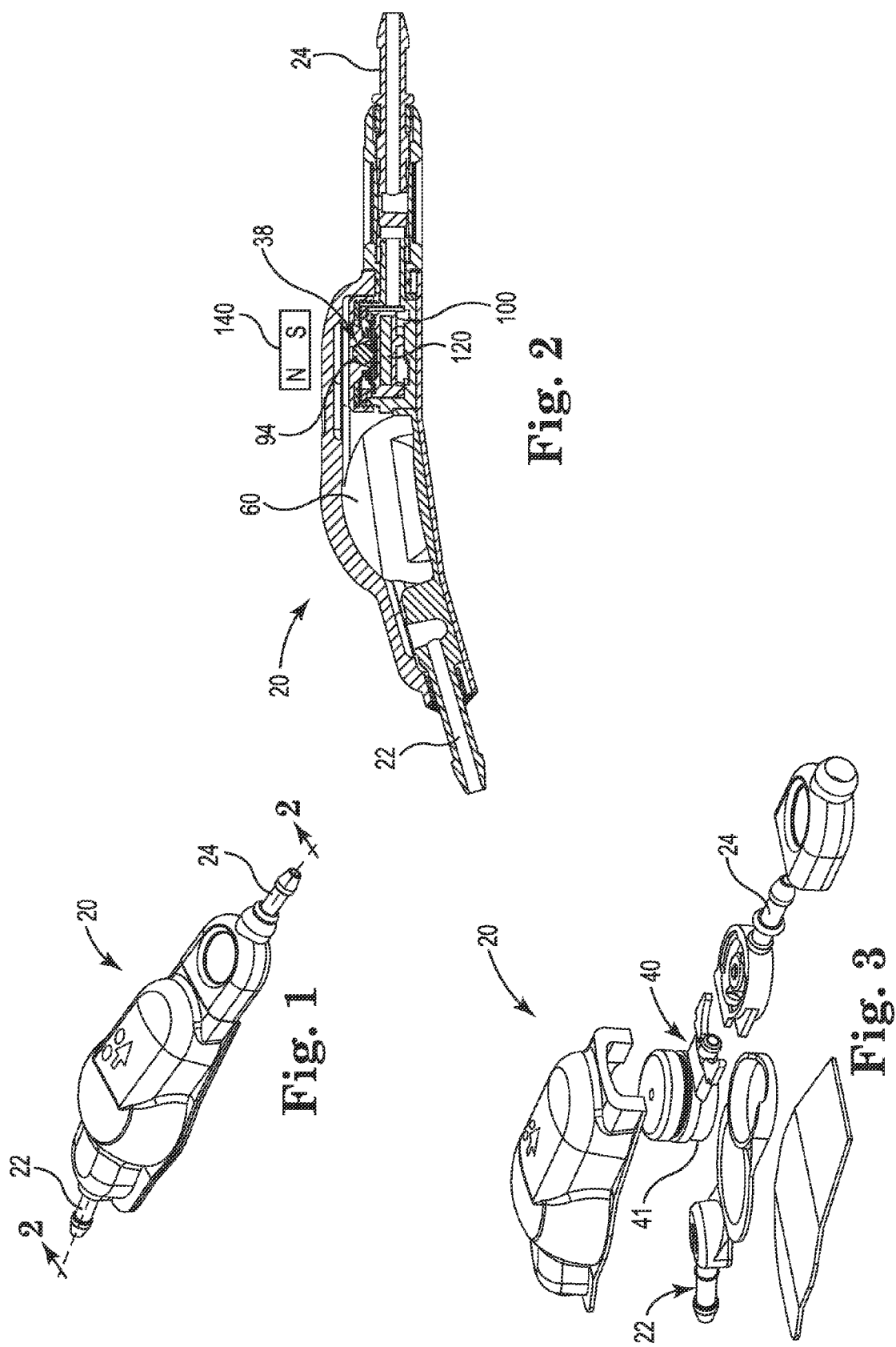

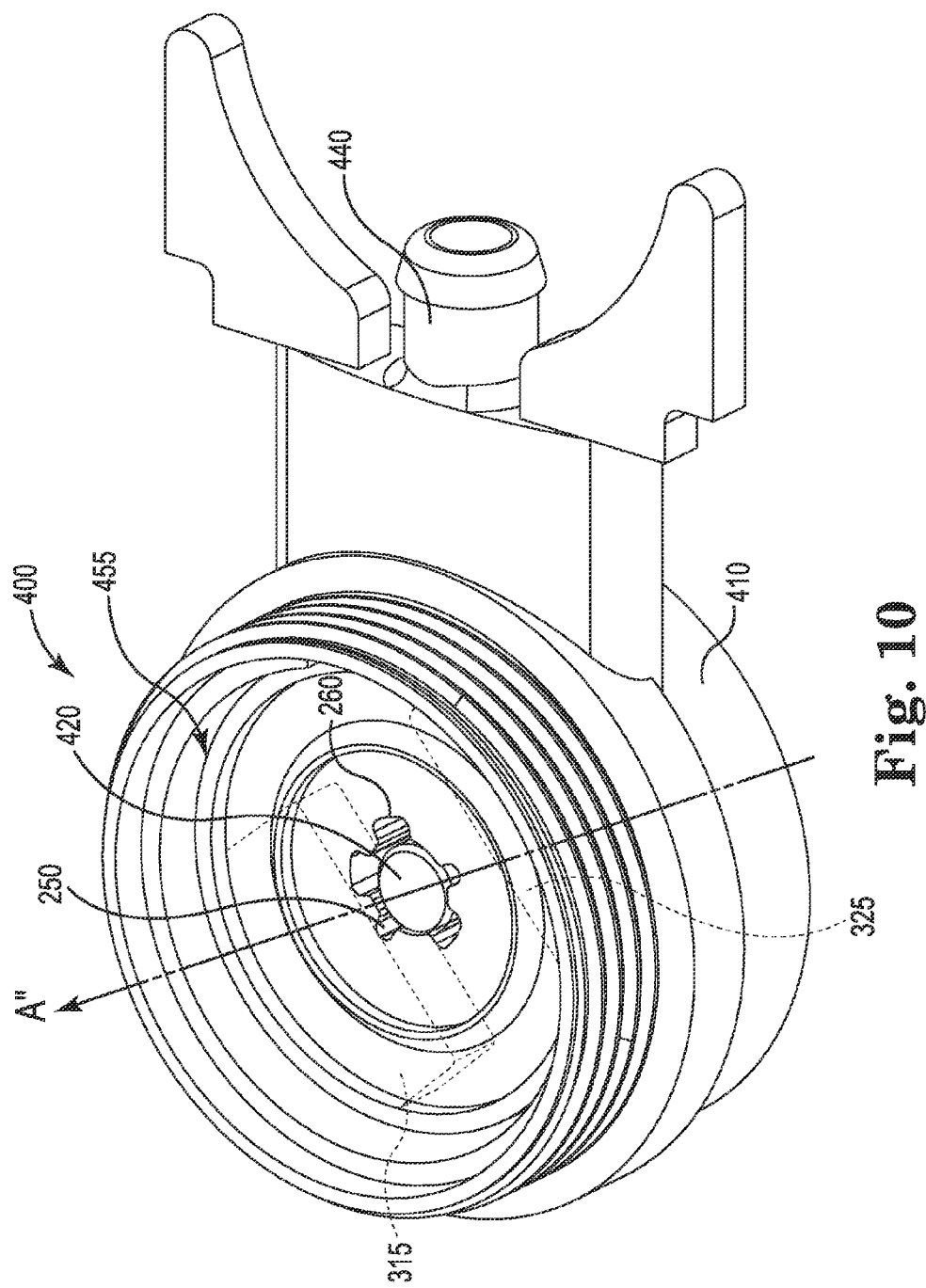

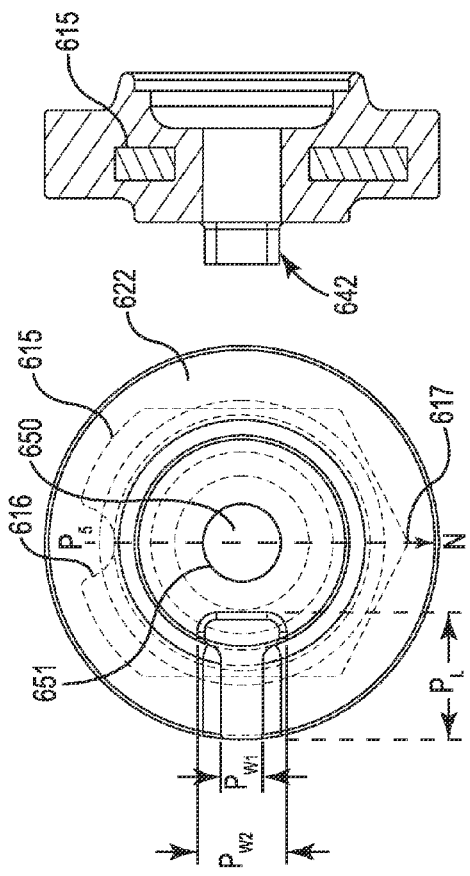
Fig. 12C
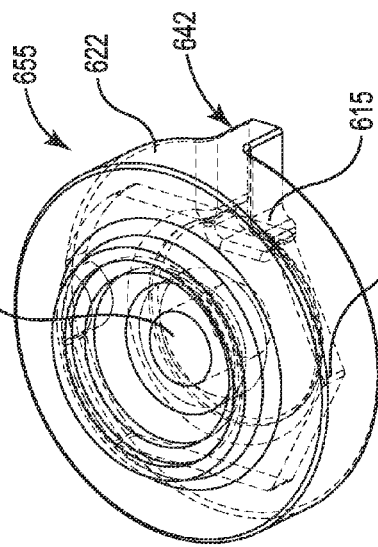
Fig. 12D
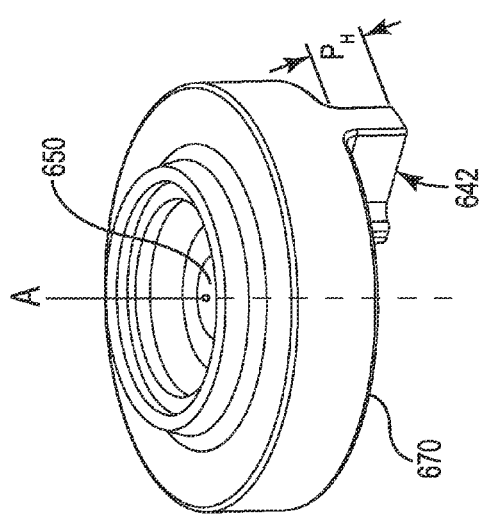
Fig. 12A
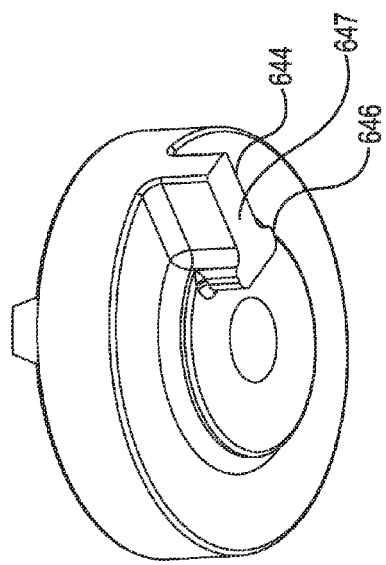
Fig. 12B
Fig. 12E

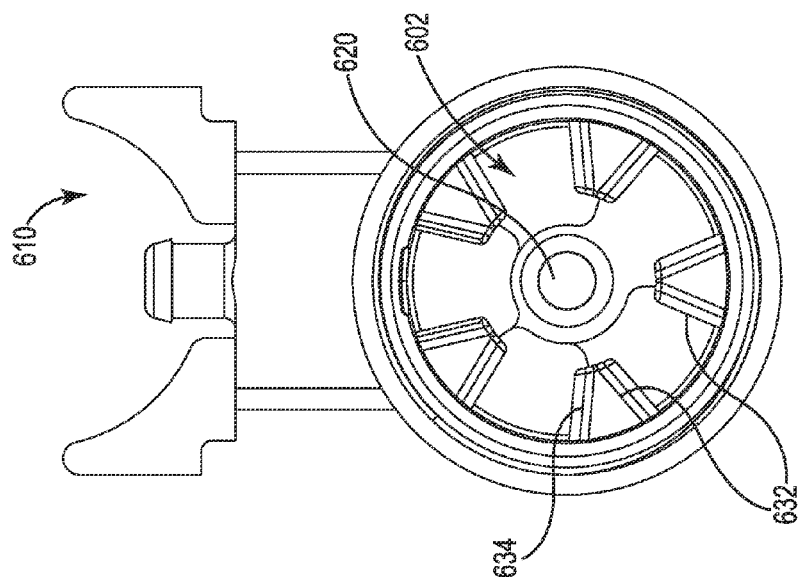
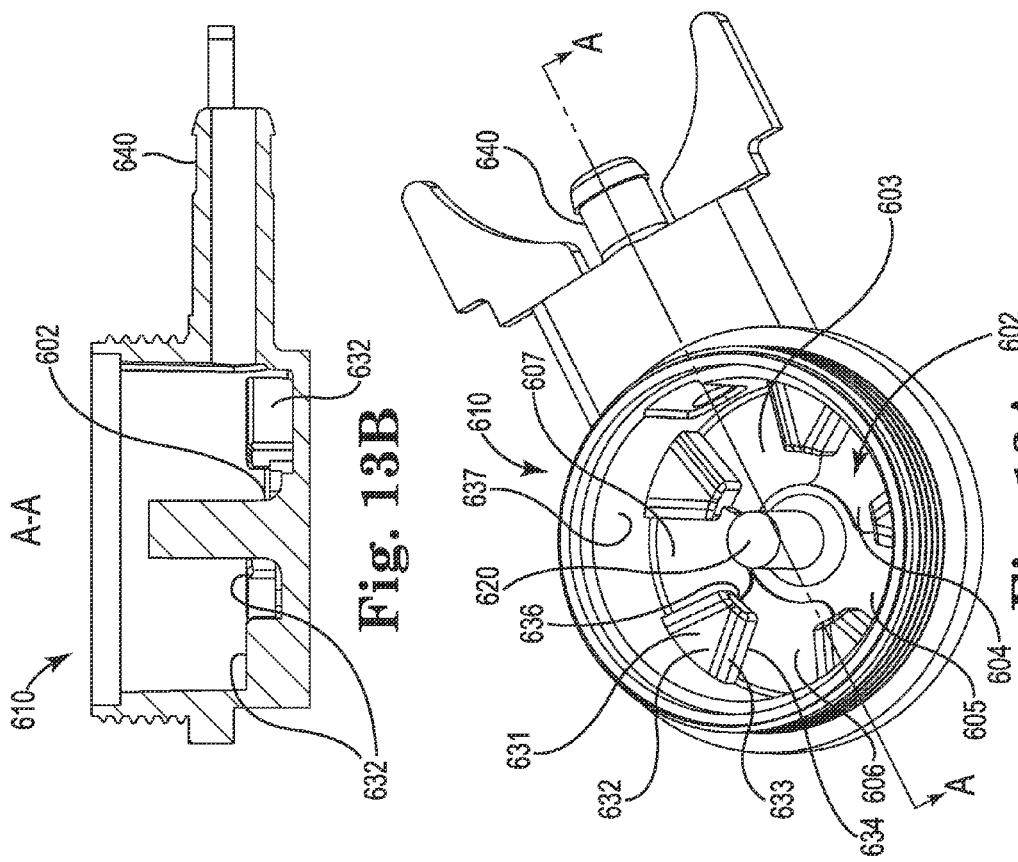

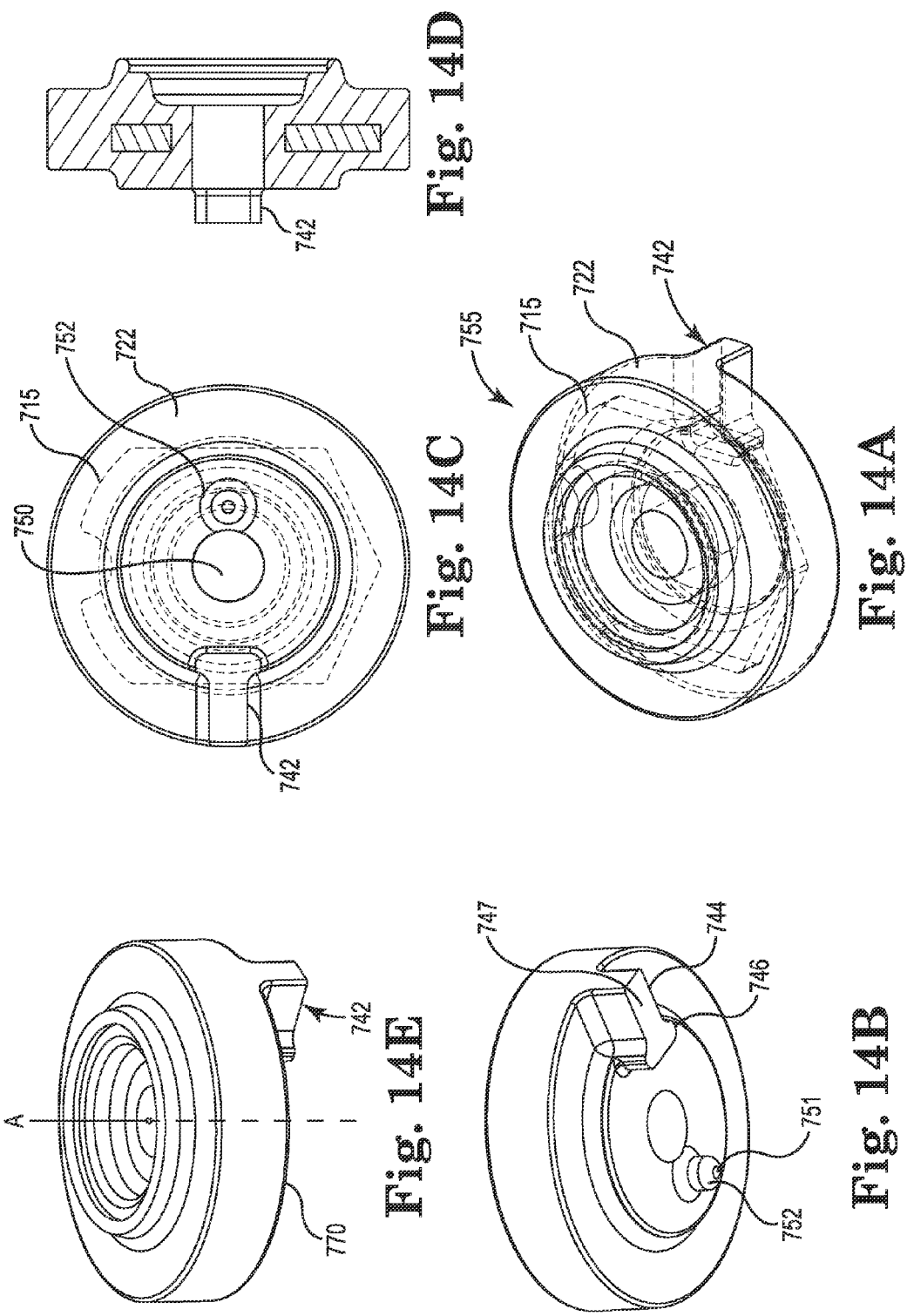

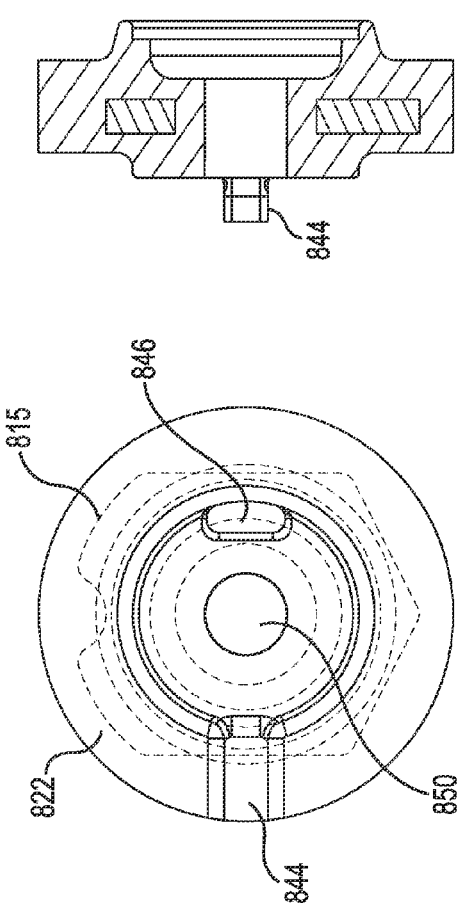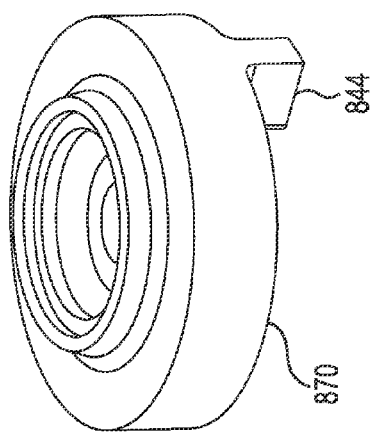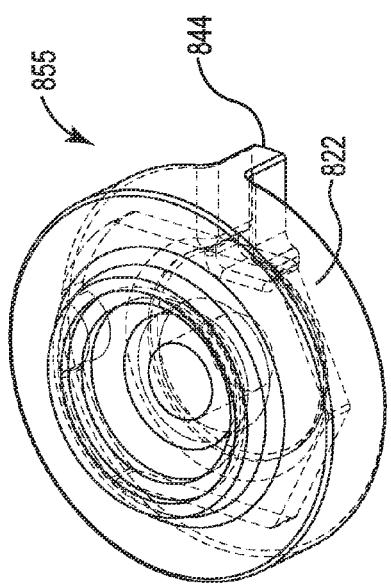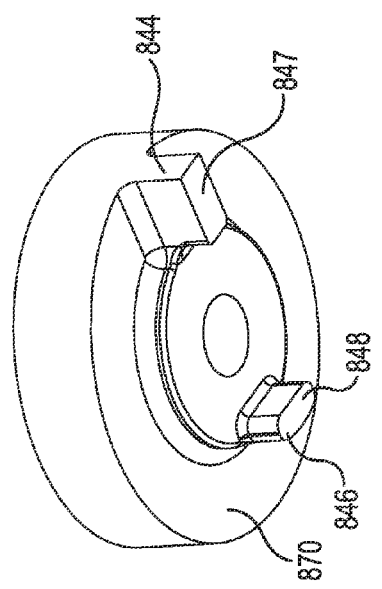

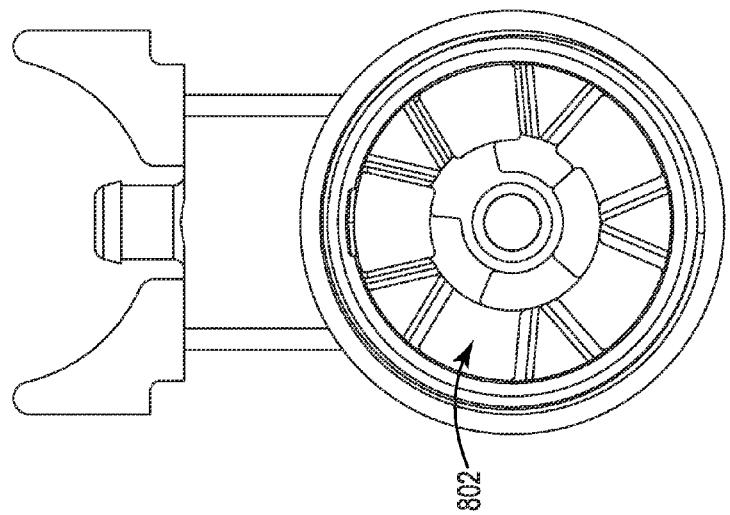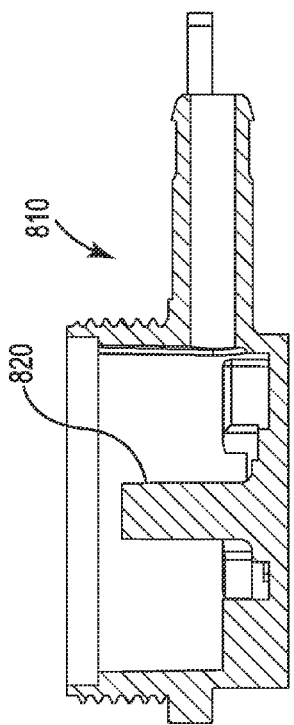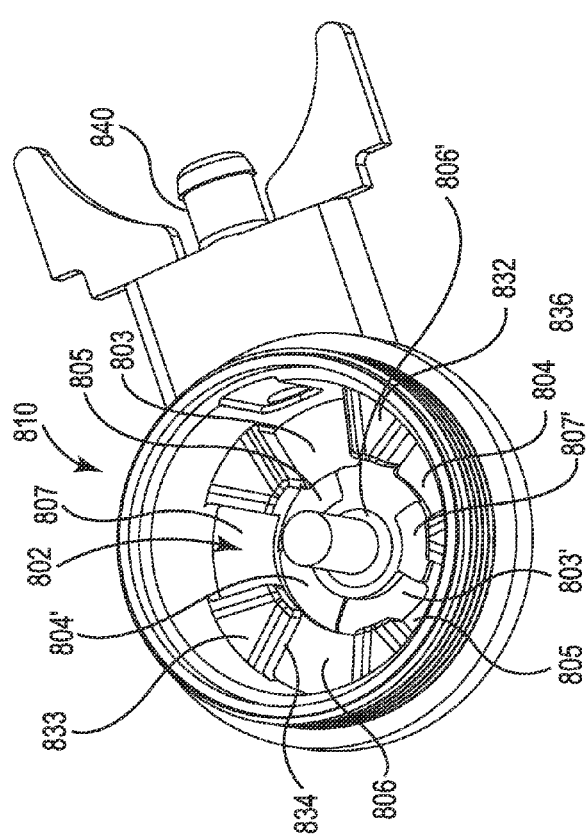

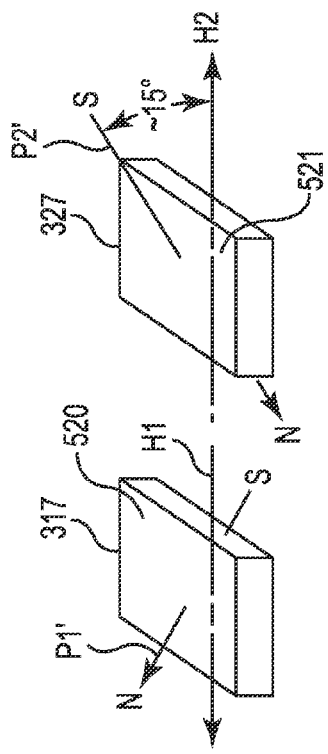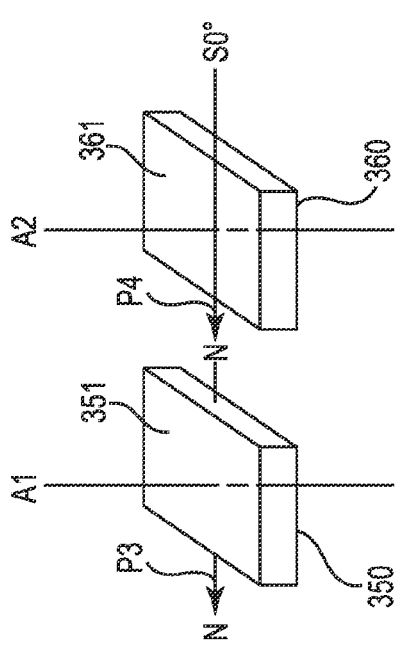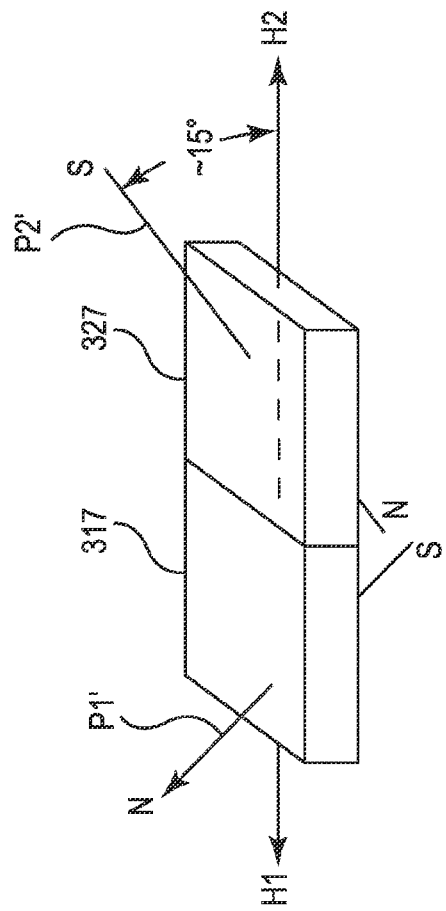
Fig. 18
Fig. 19
Fig. 20

FLUID FLOW CONTROL DEVICES, ROTORS AND MAGNETS WITH INCREASED RESISTANCE TO INADVERTENT SETTING CHANGE AND IMPROVED ACCESSORY TOOL COUPLING

CROSS REFERENCE TO RELATED APPLICATIONS

This application claims priority to U.S. Provisional Application No. 61/662,664, filed on Jun. 21, 2012, hereby incorporated by reference in its entirety.

BACKGROUND

The present disclosure relates generally to implantable physiological shunt systems and related fluid flow control devices as well as accessories for use therewith. More specifically, the present disclosure provides devices, systems and methods relating to implantable medical fluid flow control devices, rotors and magnets with increased resistance to inadvertent setting changes. The present disclosure also provides devices, systems and methods relating implantable medical fluid flow control devices, rotors and magnets which provide improved magnetic coupling to fluid flow control device accessories such as adjustment tools.

Generally, a fluid flow control device includes a one-way control valve for controlling the flow of cerebrospinal (CSF) fluid out of a brain ventricle and preventing backflow of fluid into the brain ventricle. One example of a fluid flow control device is disclosed, for example, in U.S. Pat. No. 5,637,083 entitled, "Implantable Adjustable Fluid Flow Control Valve", incorporated by reference herein in its entirety. Hydrocephalus, a neurological condition which may affect infants, children and adults, results from an undesirable accumulation of fluids, such as CSF, within the ventricles, or cavities, of the brain and which accumulation may exert extreme pressure with brain and in infants, skull deforming forces. Treatment of hydrocephalus often involves draining CSF away from the brain ventricles utilizing a drainage or shunt system including one or more catheters and a shunt valve which may generally be described as a fluid flow control device. The shunt valve, or fluid flow control device, may have a variety of configurations and may be adjustable in that the valve mechanism of the device may be set to a threshold pressure level at which fluid may be allowed to begin to flow through the valve and drain away from the brain. Fluid flow control devices may be subcutaneously implantable and percutaneously adjustable. Flow control devices may have a number of pressure settings and may be adjustable to the various pressure settings via external magnetic adjustment tools. Some fluid flow control devices are magnetic in that the devices include a magnetic rotor or rotor assembly which interacts with a valve mechanism and an adjustment mechanism to selectively adjust a valve opening pressure. The magnetic rotor or rotor assembly may magnetically couple with an external magnetic adjustment tool or tools. Magnetized rotors often include a single magnet or dual magnets arranged or configured to have aligned horizontal polarity. The magnetic adjustment tools are designed to externally (i.e., external to a patient) couple to a rotor magnet of a fluid flow control device implanted in a patient such that upon coupling, the rotor may be deliberately rotated to thereby adjust the pressure setting of the device non-invasively. Adjustment tools can include magnets which may be placed in line with the rotor magnet or magnets in order to couple to and drive the rotor externally, or through the tissue, after the valve is implanted. Typically, an adjustment tool is placed externally, for example, on the patient's head and in proximity to the implanted device. In this manner, it is possible to set the valve rotor into a desired position in a non-invasive manner.

A rotor or rotor assembly having a single magnet or dual magnets with aligned horizontal polarity may cause the magnetic rotor to be susceptible to movement or inadvertent setting adjustment by a strong nearby magnetic field since the internal magnetic elements arranged in this manner may tend to align with the external field. A magnetic rotor might thus be unintentionally adjusted when in the presence of a strong external magnetic field such as encountered in a magnetic resonance imaging (MRI) procedure, for example an MRI field of up to 3.0 Tesla. Unintentional adjustment can result in the rotor moving to a position whereby the pressure setting of the fluid flow control device is other than optimal for the particular patient. Depending upon how a valve or device (and thereby the magnetic rotor) enters the MRI, the magnetic field of the MRI equipment may work to turn (i.e., rotate) the rotor to a new setting, or, if the valve enters the MRI equipment at a 90 degree angle to the MRI magnetic field, the MRI field may work to flip (tilt) the rotor. Potential unintended adjustment may therefore require checking and/or re-adjustment via the external accessories and/or adjustment tools each time a patient is or has been in the presence of a strong external magnetic field. Therefore, the need exists for a fluid flow control device, rotor, and/or magnet which provides increased resistance to inadvertent setting changes.

Intentional adjustment, verification and indication of fluid flow control device or valve pressure settings may be accomplished via external tools and/or accessories including, for example, locator, indicator and/or adjustment tools. As described above, an adjustment tool may include a magnet or magnets for coupling to and rotating an implanted rotor assembly thereby setting a device or valve pressure threshold. However, since during use the adjustment tool is located at a distance from the implanted valve and is external to the patient, device components and/or tissue between the adjustment tool magnets and valve magnet or magnets may interfere with the magnetic coupling of the two. This interference can result in a decreased magnetic field strength making intentional adjustment of pressure settings more challenging. Therefore it may be desirable to improve or increase the magnetic coupling or magnetic field strength between an implanted fluid flow control device and related external magnetically coupleable accessories.

U.S. Pat. No. 5,643,194 to Negre describes a subcutaneous valve and device for externally setting it. Negre describes two micromagnets mounted in a rotor and locking means for locking the rotor in predetermined positions. The locking means described require internal device parts to move linearly to engage mechanical stops for locking the rotor in place. It may be desirable to avoid this type of mechanism since moving mechanical parts tend to decrease life of a product and increase mechanical wear. In addition, it is often desirable to design components which utilize or take up as little space as possible in implantable medical devices such as fluid flow control devices. The locking mechanism described by Negre may undesirably or unnecessarily utilize space for several reasons not the least of which may include by virtue of requiring the particular moving parts disclosed. Another disadvantage of this design is that biological debris is more likely to undesirably interfere with or jam the movable parts.

U.S. Patent Application Publication No. 2012/0046595 to Wilson et. al. describes an implantable adjustable valve. Wilson et. al. describe a rotor for a valve unit where rotor magnets may have axes of magnetization arranged to lie at an angle relative to an axis of rotation of the rotor purportedly to achieve improved interaction with an indicator or adjustment tool. Wilson et. al. describes the angled axes of magnetization are achieved by physically tilting the magnets within the valve assembly such that the magnets themselves lie in a plane angled with respect to a flat or horizontal planar surface of the valve. Physically tilting or angling the magnets in the manner described by Wilson et. al. may also undesirably utilize space within a device.

SUMMARY

In some embodiments the present disclosure provides a rotor assembly for an adjustable fluid flow control device comprising a base and two magnets mounted in the base where each of the two magnets are polarized in a substantially vertical orientation and are oppositely oriented with respect to one another. In some embodiments the rotor assembly may include a base comprising a central aperture and a single magnet or a plurality of magnets may be embedded in the base. An embodiment according to the disclosure may further include a cartridge assembly comprising a cartridge housing and a rotor assembly at least partially received therein. The cartridge housing may include a central rotor pivot or axle configured to engage a central aperture of a rotor assembly and about which a rotor assembly is configured to rotate. The central rotor pivot may comprise at least one spline and the rotor central aperture may comprise at least one groove which at least one groove is configured to engage the at least one spline such that rotation of the rotor assembly about the rotor pivot is inhibited upon engagement of the at least one groove with the at least one spline. In some embodiments an at least one spline comprises a plurality of splines and in some embodiments at least one groove comprises a plurality of grooves.

In some embodiments an at least one spline or each spline of a plurality of splines comprises a spline height which is less than a height of a rotor pivot and the rotor assembly is configured to lift vertically upwardly along the rotor pivot such that the at least one groove is configured to disengage an at least one spline when the rotor assembly is lifted vertically upwardly a sufficient distance or such that a lower end of the at least one groove is in spaced relation and is above an upper end of the at least one spline. The rotor assembly may be configured to rotate about the rotor pivot upon disengagement of the at least one groove with the at least one spline.

Still further embodiments according to the disclosure provide a cartridge assembly including a rotor or rotor assembly comprising a base comprising at least one notch along an outer perimeter of the base, a magnet or magnets embedded in the base, and a cartridge housing configured to at least partially receive the rotor assembly therein, where the rotor assembly is configured to rotate within the cartridge housing and wherein the rotor assembly is configured to lift vertically upwardly with respect to a bottom surface of the cartridge housing. The cartridge housing may comprise a rotor pivot about which the rotor or rotor assembly is configured to rotate. In some embodiments, the cartridge housing comprises an inner wall comprising at least one tab configured to engage the at least one notch such that rotation of the rotor assembly within the cartridge housing is inhibited upon engagement of the at least one notch with the at least one tab In some embodiments, an at least one tab comprises a height less than a height of the inner wall and the at least one tab is configured to disengage with the at least one notch when the rotor assembly is lifted such that a lower end of the at least one notch is in spaced relation and is above an upper end of the at least one tab. The rotor may be configured to rotate within the cartridge housing upon disengagement of the at least one notch with the at least one tab. In some embodiments the at least one notch comprises a plurality of notches and in some embodiments the at least one tab comprises a plurality of tabs. In some embodiments where the cartridge housing includes a rotor pivot and a plurality of notches, the rotor pivot further includes at least one spline and the rotor assembly includes at least one groove.

In some embodiments, a cartridge assembly may comprise a rotor assembly, as disclosed in any of several embodiments, where the rotor assembly is magnetically coupleable to an adjustment tool and is further configured to lift vertically upwardly upon magnetically coupling with the adjustment tool.

Some embodiments according to the disclosure provide a rotor assembly for an adjustable fluid flow control device comprising a base comprising a central vertical axis, two magnets mounted in the base, where each magnet comprises a planar surface and wherein each of the two magnets are embedded in the base such that the planar surface of each magnet lies in a plane substantially perpendicular to the central vertical axis; and wherein each magnet comprises an angle of polarization from 0 degrees to less than 90 degrees relative to the central vertical axis. Each magnet may comprise a horizontal planar surface and a horizontal magnet axis and the angle of polarization of each magnet may comprise an angle greater than 0 degrees and equal to or less than 90 degrees relative to the horizontal magnet axis. In some embodiments, the rotor assembly having magnets with angled magnetization or polarization may comprise two angularly polarized magnets coupled together to form a single rotor magnet.

Systems according to the disclosure include an implantable fluid flow control device comprising an inlet and an outlet spaced from the inlet, a valve mechanism for controlling the flow of fluid from the inlet to the outlet where the valve mechanism comprises a ball and spring configured to interact with a rotor assembly and a fixed dual concentric stair-step array. The rotor assembly may be configured to rotate relative to the stair-step array in response to an externally applied magnetic field wherein such rotation raises or lowers the rotor assembly with respect to the stair-step array and wherein the rotor assembly comprises a base comprising a two magnets mounted in the base where each of the two magnets may be polarized in a substantially vertical or vertical orientation oppositely oriented with respect to one another or may be polarized at an angle with respect to a horizontal magnet axis.

Systems according to the disclosure include an implantable fluid flow control device comprising an inlet and an outlet spaced from the inlet, a valve mechanism for controlling the flow of fluid from the inlet to the outlet where the valve mechanism comprises a ball and spring configured to interact with a rotor assembly and a fixed dual concentric stair-step array. The rotor assembly may be configured to rotate relative to the stair-step array in response to an externally applied magnetic field wherein such rotation raises or lowers the rotor assembly with respect to the stair-step array and wherein the rotor assembly comprises a base comprising a magnet mounted in the base and a mechanical stop configured to inhibit unintentional rotation of the rotor assembly when the device is in the presence of a strong magnetic field and further configured to allow intentional rotation of the rotor assembly to adjust a pressure setting of the device.

Methods according to the disclosure may comprise methods of manufacturing or producing magnets with angled polarization or magnetization whereby magnets comprising angled magnetization may be manufactured or produced by machining magnetic material along a material grain which comprises an angle equal to the desired angle of polarization of the magnet.

BRIEF DESCRIPTION OF THE DRAWINGS

FIG. 1 is a perspective view of a subcutaneously implantable and percutaneously adjustable fluid flow control device useful with the present disclosure.

FIG. 2 is a side cross-sectional view of the fluid flow control device of FIG. 1.

FIG. 3 is an exploded view of the device of FIG. 1.

FIG. 10 is a three-dimensional view of a cartridge assembly according to an embodiment.

FIGS. 12A-12E depict a rotor assembly according to an embodiment.

FIGS. 13A-13C depict a cartridge housing according to an embodiment.

FIGS. 14A-14E depict a rotor assembly according to an embodiment.

FIGS. 16A-16E depict a rotor assembly according to an embodiment.

FIGS. 17A-17C depict a cartridge housing according to an embodiment.

FIG. 18 is an illustration of conventional magnet polarity for magnets useful with embodiments according to the disclosure.

FIG. 19 is an illustration of angled magnet polarity for magnets useful with embodiments according to the disclosure.

FIG. 20 is an illustration of angled magnet polarity for magnets useful with embodiments according to the disclosure.

DETAILED DESCRIPTION

Figure 4:
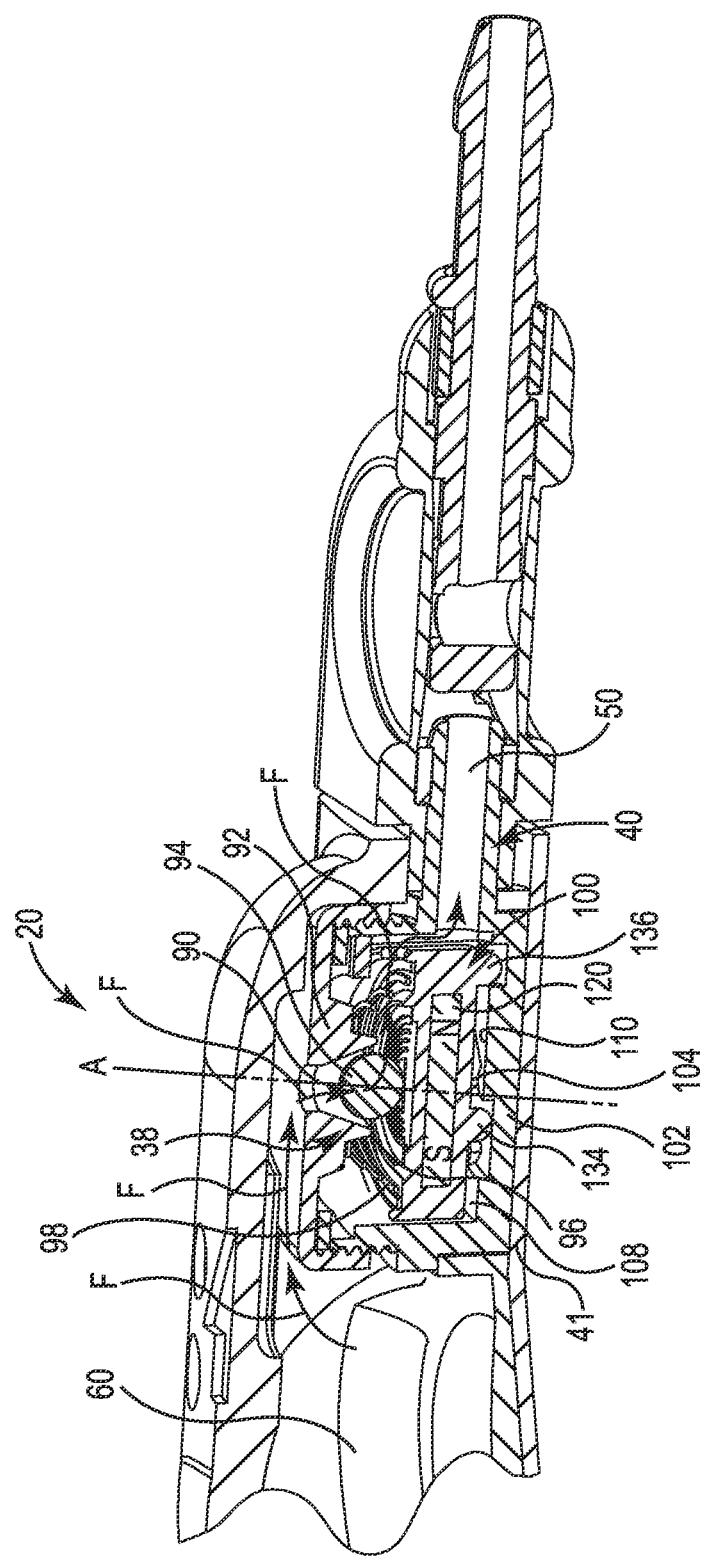
FIG. 4 is a three-dimensional cross-section of a portion of the device of FIG. 2.

FIG. 1 depicts a fluid flow control device 20 which may be useful with devices and assemblies according to the present disclosure. Fluid flow control device 20 may be subcutaneously implanted in a patient (not shown) and may be percutaneously adjustable. Fluid flow control device 20 comprises an inlet connector 22 and an outlet connector 24, each for receiving one end of a piece of surgical tubing (not shown). Inlet 22 is configured to fluidly connect to a catheter (not shown) which may be inserted through a patient's skull into a brain ventricle containing cerebrospinal (CSF) under pressure. The outlet connector 24 is configured to fluidly connect to a distal catheter which serves to direct CSF to another location in the patient's body. FIG. 2 depicts a cross-sectional view of the fluid flow control device of FIG. 1 taken along section 2-2. Fluid flow control device 20 includes a fluid reservoir 60, a valve mechanism 38 and a rotor assembly 100 described in further detail with reference to FIG. 4. Also shown in FIG. 2 is an external tool 140 described further herein below.

Figure 5:
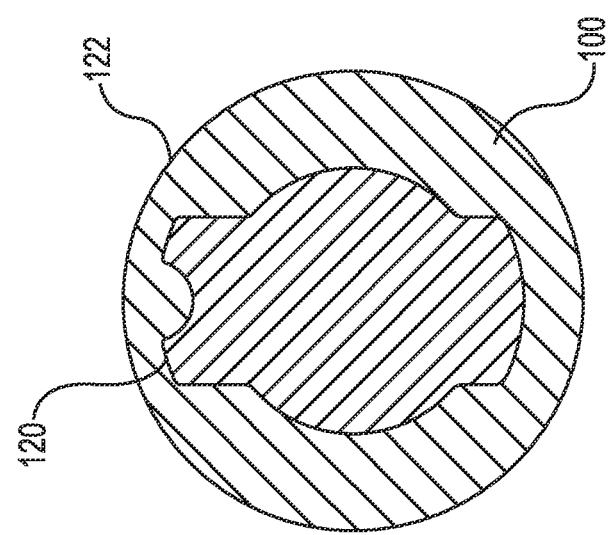
FIG. 5 is a cross-sectional top view of rotor assembly and magnet useful with the present disclosure.

FIG. 3 depicts an exploded view of the fluid flow control device 20 of FIG. 1. Fluid flow control device 20 comprises a cartridge assembly 40 including a cartridge housing 41, for housing a rotor assembly 100 (FIG. 2). FIG. 4 depicts a three-dimensional partial view of the cross section of FIG. 2. Valve mechanism 38 provides means for controlling fluid flow "F from the inlet connector 22 to the outlet connector 24. More particularly, the valve mechanism 38 controls fluid flow "F" from a flushing reservoir 60 to a cartridge outlet fluid passageway 50. The valve mechanism 38 includes a ball 94 which seats against a valve seat 92 to control the flow of fluid through a fluid passageway 90. A pressure spring 96 is disposed below and in contact with the ball 94 to bias the ball 94 against the valve seat 92 to keep passageway 90 closed until a fluid pressure differential between the inlet 22 and outlet 24 exceeds a selected or desired valve opening pressure. Pressure spring 96 is supported at an end opposite the ball 94 by an first upper surface 98 of rotor assembly 100. Rotor assembly 100 includes a magnet 120 or may include any of the magnets described herein below. Magnet 120 is provided within a base 122 which defines upper and lower surfaces 98 and 104. The magnet or magnets 120 may be embedded or encapsulated in base 122. FIG. 5 shows a top plan view of rotor assembly 100 including a base 122 with a single rotor magnet 120 embedded therein.

Returning to FIG. 4, the lower surface 104 of rotor assembly 100 may include a single or multiple projections protruding from the lower surface 104. For example, the lower surface 104 may include a single or multiple legs, tabs or feet. FIG. 4 depicts inner and outer legs 134 and 136 depicted in FIG. 4, other configurations of a projection or projections are described below. Regardless, the projection or projections are configured to bear against either a single stair step array 602 (FIG. 13A) or a selected one of a plurality of inner and outer steps 108 and 110 of a fixed dual concentric stair-step array 102. Rotor assembly 100 is configured to rotate in response to an applied magnetic field as described below.

The single 602 (FIG. 13A) or dual concentric stair-step array 102 allows adjustment of the amount of bias applied to the ball 94 in order to vary the selected valve mechanism 38 opening pressure. Lower surface 104 of the rotor assembly 100 is supported by the stair-step array 102, 602 which interacts with the projection or projections (i.e., legs 134, 136 in FIG. 4) projecting from surface 104 to vary the relative height of the rotor assembly 100 with respect to the valve mechanism 38. The dual concentric stair-step array 102 shown, for example in FIG. 4, 9A, comprises a plurality of inner steps 108 surrounding the rotor pivot 106 and a corresponding plurality of outer steps 110 extending peripherally about the inner steps 108. The inner and outer steps 108 and 110 are constructed so that those steps opposite to one another with respect to a central rotor axis A, subtend the same arch and are located at the same level.

The rotor assembly 100 includes a rotor magnet 120 which may include a single magnet (as shown) or dual magnets with horizontally aligned polarity or may comprise any of the magnets described herein below. An external magnetic tool or accessory 140 (FIG. 2) may be used to adjust, locate or verify position of the rotor assembly 100. Inner and outer legs 134, 136 are illustrated in FIGS. 2 and 4 as comprising nubs however, legs 134 and 136 may comprise other configurations such as projections having various shapes or may include other projections as described above.

It is to be understood that any of the fluid flow control device elements disclosed or described herein and/or depicted in the various embodiments herein including rotor assemblies, cartridges, cartridge housings, bases, magnets, and/or other housings or assemblies useful therewith, may be useful with fluid flow control device 20 or with any of the elements described herein. As but one example, rotor assembly 655 and cartridge housing 610 (FIGS. 12A, 13A) may be used in lieu of or in place of rotor assembly 100 and cartridge housing 41 of fluid flow control device 20. As another example, magnets 315 and 325 (FIG. 11) could be used in lieu of or in place of magnet 120 or in place of magnets 300 and 310 (e.g., FIG. 8) and so on. Likewise, any of the fluid flow control device elements disclosed herein may be useful in a variety of other fluid flow control devices (not depicted).

Figure 6A:
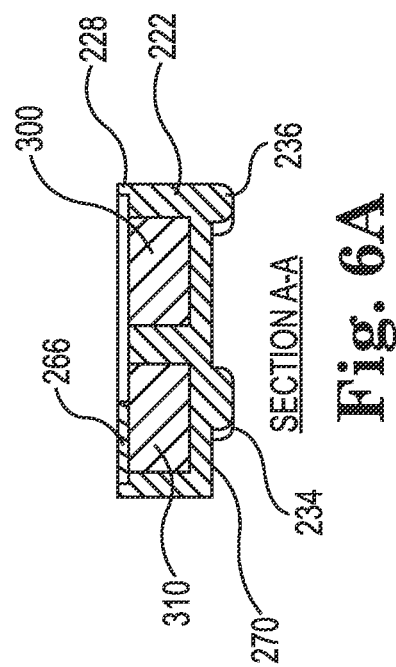
FIG. 6A is a cross-sectional side view of the rotor assembly of FIG. 6.
Figure 6:
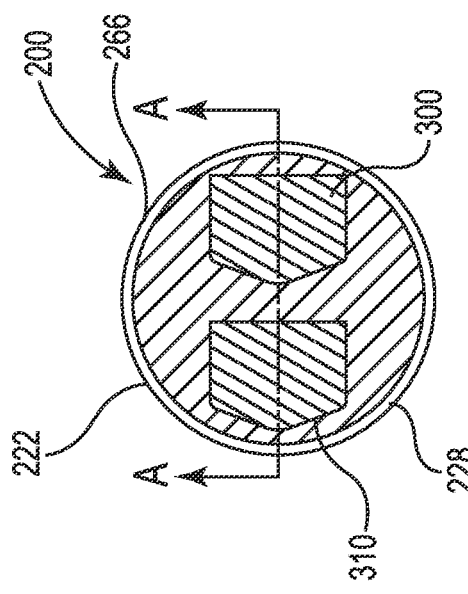
FIG. 6 is a cross-sectional top view of a rotor assembly for a fluid flow control device according to an embodiment.
Figure 9A:
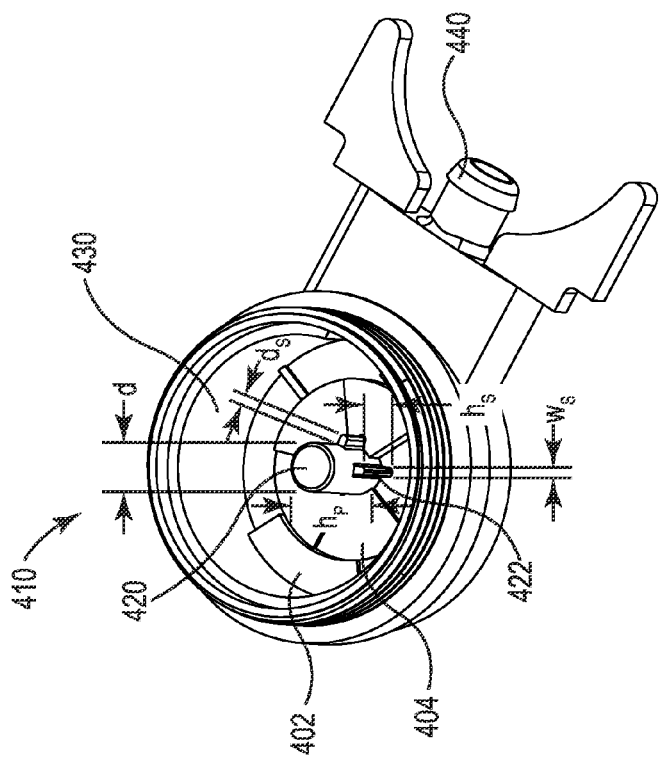
FIG. 9A is a three-dimensional view of a cartridge housing according to an embodiment.

FIG. 6 depicts a cross-sectional top plan view of a rotor assembly 200 according to an embodiment. Rotor assembly 200 includes a housing or base 222 and two magnets, a first magnet 300 and a second magnet 310, embedded in the base 222. An outer ring 228 defines a lip around the circumference of the base 222. Outer ring 228 is more clearly depicted in FIG. 6A which is a cross-sectional side view of the rotor assembly 200 of FIG. 6. Ring 228 may include a lock-step tab 266 which may interact with a portion of a fluid flow control device to function as a stop to limit rotation of the rotor assembly 200 relative to the stair-step array e.g., 402 (FIG. 9A) to less than 360°. However, ring 228 may be provided without a lock-step tab 266 in some embodiments. Inner legs 234 and outer legs 236 illustrated in the form of nubs, depend from a lower surface 270 of the base 222 and are configured to interact with a portion of a fluid flow control device 20 such as with a dual concentric stair step array e.g., 402 (FIG. 9A).

Figure 7:
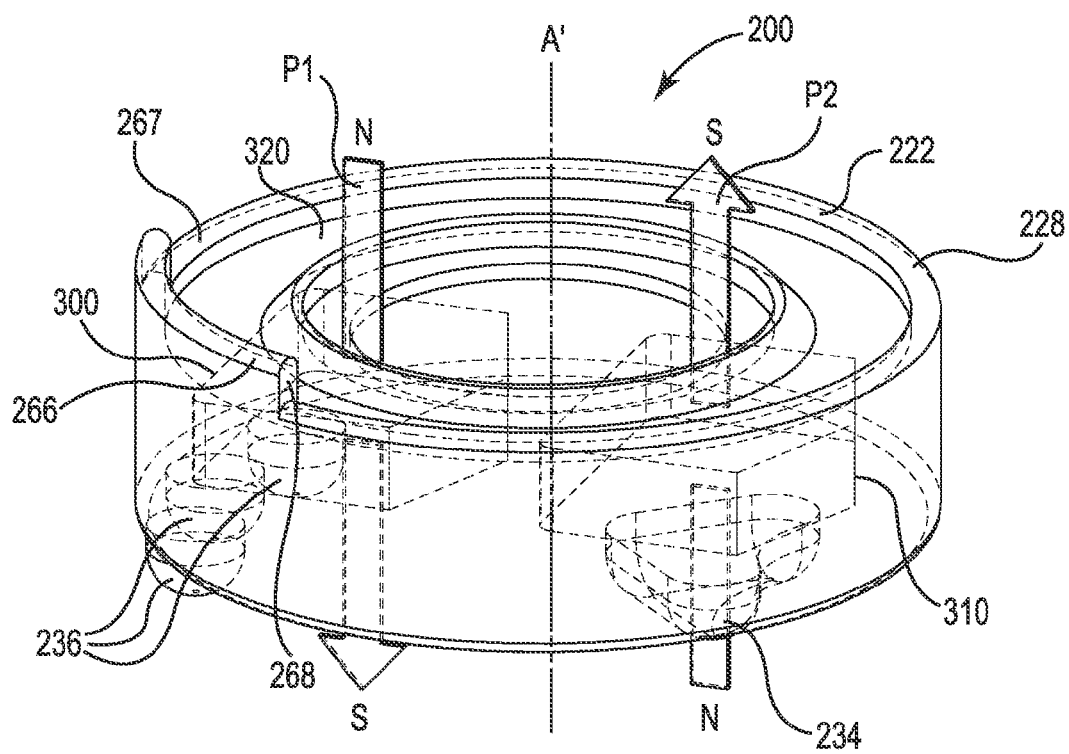
FIG. 7 is a three-dimensional view of the rotor assembly of FIGS. 6 and 6A showing two rotor magnets in phantom, according to an embodiment.

FIG. 7 is a three-dimensional view of rotor assembly 200 in which lock-step tab 266 can be seen projecting from outer ring 228. Inner and outer legs 234, 236 are depicted partially in phantom. Magnets 300, 310 are also shown in phantom in base 222. Magnets 300, 310 may be mounted in or embedded in base 222 such that magnets 300, 310 are positioned at various distances relative to one another within base 222. Magnets 300, 310 may be positioned in very close proximity such that magnets 300, 310 are nearly in contact or are in contact with one another. Likewise, magnets 300, 310 may be positioned with space (as shown) between magnets 300, 310.

First and second magnets 300, 310 are each shown as comprising a five-sided polygonal shape (in a top plane or top cross-sectional view) with approximately straight edges or sides. However, magnets 300, 310 may comprise any shape or combination of shapes including circular, semi-circular, spherical, hemispherical, elliptical, or polygonal, as but several examples. First magnet 300 and second magnet 310 may comprise substantially similarly shaped configurations and sizes or may each comprise a different one of the several shapes described above. Regardless, both magnets 300 and 310 are polarized in a vertical or substantially vertical direction i.e., substantially parallel to a central vertical rotor axis A' of rotor assembly 200 and polarity P1, P2 of magnets 300 and 310, respectively, is oppositely aligned. Thus, as depicted by arrows P1 and P2, magnets 300 and 310 each comprise vertical polarity and comprise opposite or reverse polarity with respect to one another.

Figure 8:
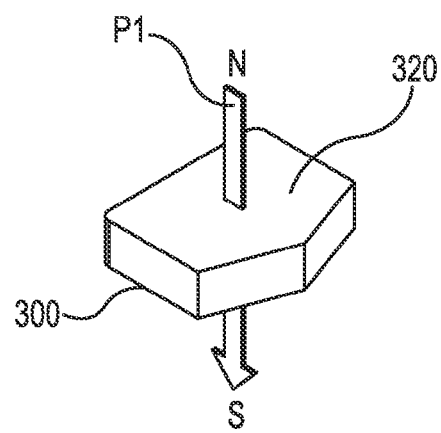
FIG. 8 is a three-dimensional view of a rotor magnet according to an embodiment.

FIG. 8 shows a three-dimensional view of one magnet 300 apart from rotor assembly 200 depicting vertical polarity as described above. Magnet 300 is polarized in a vertical or substantially vertical direction indicated by arrow P1. Polarity P1 is vertical or substantially vertical with respect to a horizontal upper planar surface 320 of magnet 300.

A rotor assembly (e.g., 200) comprising magnets 300, 310 which comprise vertical polarity P1, P2 in the manner disclosed may tend to resist aligning with a strong or nearby external magnetic field, such as during a magnetic resonance imaging (MRI) procedure since opposite alignment of the polarity P1, P2 of the magnets 300 and 310 effectively cancels the net tendency of the magnets 300, 310 (and therefore the rotor or rotor assembly) to align with the external field. Thus, inadvertent pressure setting changes may be minimized or avoided while deliberate adjustment may still be carried out. Intentional or deliberate adjustment of the rotor assembly 200 to vary a valve opening pressure may be accomplished using an external adjustment tool (e.g., 140, FIG. 2) that simultaneously presents a tool magnet (not shown) comprising polarity configured in a complementary arrangement to the rotor assembly magnets 300, 310.

With reference between FIGS. 9A and 10, alternative embodiments of a rotor assembly and cartridge assembly will be described. FIG. 9A depicts a cartridge assembly 400 for receiving a rotor assembly 455. As shown in FIG. 9A, cartridge housing 410 includes a cavity 430 configured to receive at least a portion of rotor assembly 455 whereby the cartridge housing 410 and rotor assembly 455 form a cartridge assembly 400 as depicted in FIG. 10. Cartridge housing 410 includes a bottom surface 404 comprising a fixed dual concentric stair-step array 402 similar to stair-step array 102 described above. A central rotor pivot or axle 420 is configured to engage a central aperture 250 of rotor assembly 455 such that rotor assembly 455 may rotate about central rotor pivot 420 when rotor assembly 455 is positioned at various axial locations along central rotor pivot 420. Inclusion of a central rotor pivot 420 may help to locate the rotor assembly 455 within cavity 430 and thus rotor pivot 420 aids in controlling the position of rotor assembly 455. In addition, central rotor pivot 420 includes a central vertical pivot axis A" and may comprise at least one spline 422. Central rotor pivot 420 may comprise any number of splines 422 i.e., may comprise a plurality of splines, for example two or more splines 422 with two splines shown in FIG. 9A. Splines 422 comprise a spline height "$h_s$", a spline width, "$w_s$" and a spline depth, "$d_s$". Spline height "$h_s$" may be less than a height "$h_p$" of central rotor pivot 420 and spline width "$w_s$" and depth "$d_s$" may be any width or depth and may advantageously be small relative to a diameter "d" of central pivot 420. Notwithstanding the above, in some embodiments, spline width "$w_s$" and/or spline depth "$d_s$" may be equal to or larger than rotor pivot diameter "d".

Where central rotor pivot 420 comprises more than one spline 422, the spline height "$h_s$" of each of the plurality of splines 422 may be the same or different. In other words, the height "$h_s$" of splines 422 may be varied. The spline or splines 422 are configured to engage an at least one groove 260 on rotor assembly 455 (FIG. 10) when the central aperture 250 of rotor assembly 455 is slid over the central rotor pivot 420 such that rotor assembly 455 is positioned at least partially in cavity 430 of cartridge housing 410. As indicated above, coupling of the rotor assembly 455 with cartridge housing 410 creates a cartridge assembly 400. Cartridge assembly 400 is configured for use with a fluid flow control device such as fluid flow control device 20. The cartridge assembly 400 may be positioned within a fluid flow control device such that the rotor assembly 455 interacts with a valve mechanism 38 (FIG. 1) to control the flow of cerebrospinal fluid in a patient's brain. A cartridge fluid outlet 440 is therefore configured to allow passage of CSF beyond the valve mechanism 38 and out of the device.

As depicted in FIG. 10, rotor assembly 455 includes magnets 315 and 325 where magnets 315 and 325 may comprise rounded or curved sides (not shown). In this embodiment, magnets 315 and 325 are positioned in spaced relation about central aperture 250 of rotor assembly 455 and thus are spaced about central rotor pivot 420 when rotor assembly 455 is positioned within cartridge housing 410 as shown. Magnets 315 and 325 may be similar to magnets 300 and 310 described above such that magnets 315 and 325 comprise substantially opposed vertical polarity. However, magnets 315 and 325 may comprise horizontal polarity (e.g., described with reference to FIGS. 2, 18) or may comprise a single magnet or magnets comprising angled polarization as described more fully herein below with respect to FIGS. 19-21. Additionally, rotor assembly 455 may comprise a single magnet (not shown) with a magnet aperture (not shown) for coupling to the rotor pivot 420.

Rotor assembly 455 comprises at least one groove 260 in or along central aperture 250 and may comprise any number of grooves 260 i.e., may comprise a plurality of grooves, for example five grooves 260 as shown in FIGS. 9A and 10. Each groove 260 may have a size and shape which varies from one groove 260 to another, however, each groove 260 is configured to engage (e.g., via sliding over) each spline 422 of central rotor pivot 420. The number of splines 422 and number of grooves 260 may differ, however, it may be desirable to include at least as many grooves 260 as splines 422, i.e., there may or may not be more grooves 260 than splines 422.

Figure 9B:
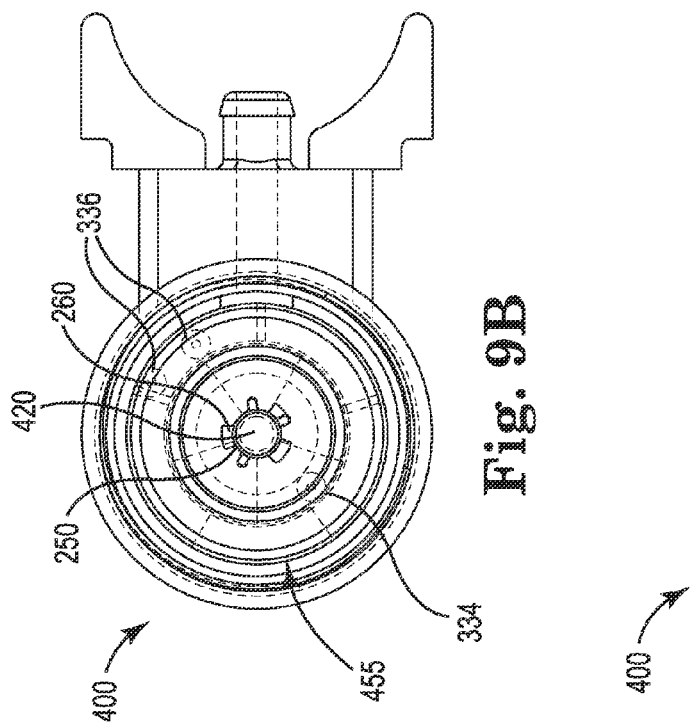
FIG. 9B is a top view of the cartridge assembly of FIG. 10.
Figure 9C:
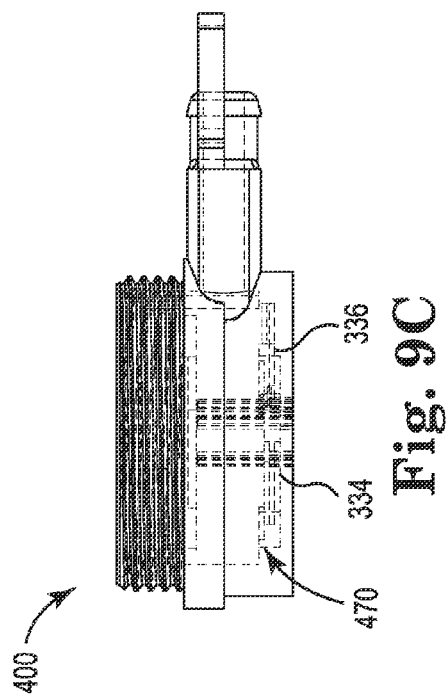
FIG. 9C is a side view of the cartridge assembly of FIG. 9B with portions of the rotor assembly and cartridge housing shown in phantom

The rotor assembly 455 is configured to be placed at least partially within cartridge housing 410 whereby the groove or grooves 260 are configured to engage the spline or splines 422 such that inner and outer leg or legs 334 and 336 depending from lower surface 470 (FIGS. 9B and 9C) of rotor assembly 455 are adjacent to, in close proximity, or in contact with the bottom surface 404 of cartridge housing 410. As a point of reference, when legs 334, 336 are in contact with the bottom surface 404, legs 334, 336 are in contact with the dual concentric stair step array 402. Regardless of the proximity of surfaces 470 and 404, as long as a groove 260 at least partially slides over or engages a spline 422, rotor assembly 455 will be inhibited from rotating about central rotor pivot 420. Thus, the at least one groove 260, or plurality of grooves, is configured to engage the at least one spline 422, or plurality of splines, such that rotation of the rotor assembly 455 about the central rotor pivot 420 is inhibited upon engagement. In this regard, the spline 422 and groove 260 configuration acts as a mechanical stop prohibiting inadvertent or undesired rotation of rotor assembly 455 about central rotor pivot 220. This type of mechanical stop may be desired for example when, as described above, a fluid flow control device 20 (or rotor, rotor assembly or magnet of a device) is in the presence of an external magnetic field strong enough to cause alignment of the rotor assembly 455 with the external field but for the mechanical stop.

If rotation of the rotor or rotor assembly is desired, i.e., deliberate adjustment is desired or required, the rotor assembly 455 is configured to lift vertically or upwardly along the rotor pivot 420. When the rotor assembly 455 is lifted vertically (upward) such that a lower end 262 of the at least one groove 260 is in spaced relation and is above an upper end 423 of the at least one spline 422, the at least one groove 260 disengages the at least one spline 422 whereby disengagement allows the rotor assembly 455 to freely rotate about the rotor pivot 420. The freedom to rotate about the rotor pivot 420, as described above, allows adjustment of the valve setting.

Figure 11:
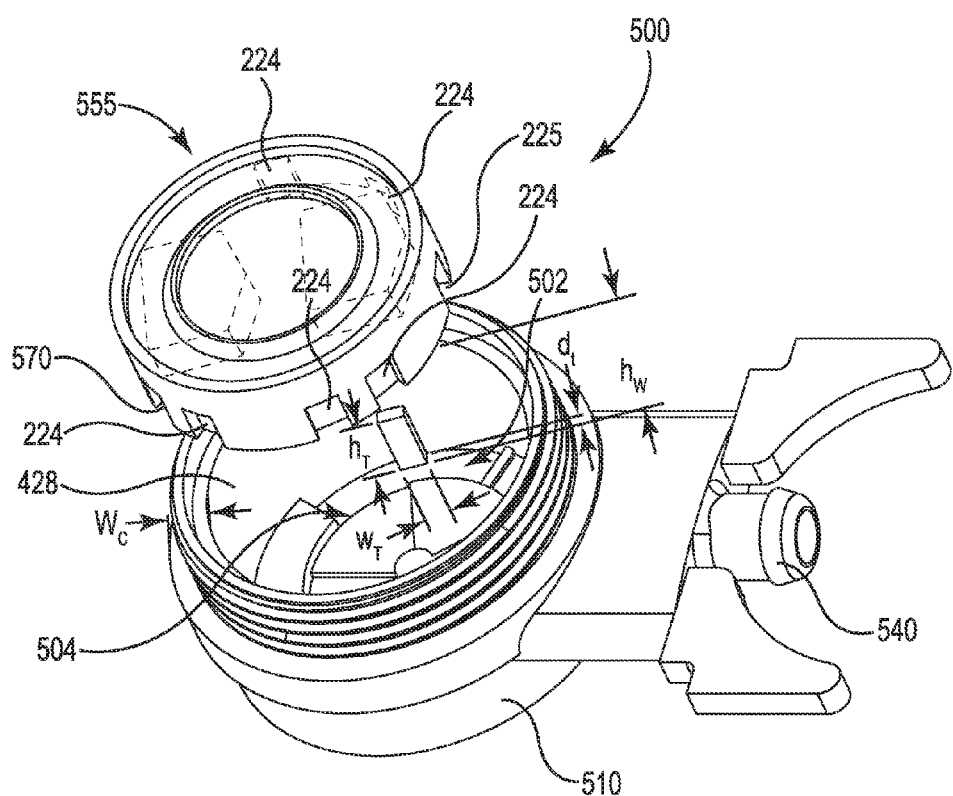
FIG. 11 is a three-dimensional exploded view of a cartridge assembly according to an embodiment.

FIG. 11 depicts an exploded view of another embodiment of a cartridge assembly, namely cartridge assembly 500. Cartridge assembly 500 includes a cartridge housing 510 comprising a cartridge fluid outlet 540 similar to fluid outlet 440 described above. Likewise, housing 510 comprises a fixed, dual concentric stair-step array 502 similar to stair-step arrays 102 and 402 described above. Rotor assembly 555 may comprise any of the magnets described herein above and may for example comprise a single magnet or two magnets where the magnet or magnets may comprise vertical, substantially vertical or horizontal polarity and may comprise oppositely aligned vertical or angled polarity described with reference to FIGS. 19-21. Two outer legs 436 are shown in phantom and are similar to legs 236 and 336 described above. Cartridge housing 510 as depicted does not include a central rotor pivot as described above with reference to cartridge housing 410, however, cartridge housing 510 may comprise a rotor pivot (not shown) similar to central rotor pivot 420 (FIG. 10). Likewise, a central rotor pivot (not shown) may comprise at least one or a plurality of splines and/or grooves as described above with reference to FIGS. 9A-10.

Housing 510 comprises at least one tab 424 on or adjacent an inner wall 428 of housing 510. Housing 510 may comprise any number of tabs 424, i.e., cartridge housing 510 may comprise a plurality of tabs 424, for example two or more tabs 424, with two tabs being shown in FIG. 11. Tabs 424 may comprise a variety of shapes, sizes and configurations, the rectangular tab shown in FIG. 11 as but one exemplary embodiment. Tabs 424 comprise a tab height "$h_t$", a tab width "$w_t$" and a tab depth "$d_t$" where "$h_t$" may be less than a height "$h_w$" of inner wall 428 and "$w_t$" and/or "$d_t$" may be relatively small compared to a width "$w_c$" of cartridge housing wall 411. Maintaining a relatively small width and/or depth "$w_t$", "$d_t$" of tabs 424 may advantageously require or consume the least or minimal amount of space in the cartridge assembly 510 which may be desirable for reasons described herein above. Accordingly, tabs may be considered low profile. Notwithstanding the above, alternatively, tab width "$w_t$" and or depth "$d_t$", may be equal to or greater than cartridge wall width "$w_c$".

Where cartridge housing 510 comprises more than one tab 424, the tab height "$h_t$" of each of the plurality of tabs 424 may be the same or different. In other words, the height "$h_t$" of tabs 424 may be varied. The tab or tabs 424 are configured to engage an at least one notch 224 on the perimeter of rotor assembly 555 when the rotor assembly 555 is positioned at least partially within cavity 430' of housing 510. The at least one notch 224 may comprise any number of notches 224, i.e., may comprise a plurality of notches, for example nine notches 224 as shown (some in phantom) in FIG. 14. Each notch 224 may comprise a variety of size and shapes which may vary from one notch 224 to another, however, each notch 224 is configured to engage (e.g., via sliding over) each tab 424 of cartridge housing 510. The number of tabs 424 and notches 224 may differ, however, it may be desirable to include at least as many notches 224 as tabs 424, i.e., there may be more notches 224 than tabs 424. Rotor assembly 555 is configured to be placed at least partially within cartridge housing 510 whereby the at least one notch 224 is configured to engage the at least one tab 424 such that a lower surface 570 (or inner and outer leg or legs 434, 436 depending from lower surface 570) of rotor assembly 555 is adjacent to, in close proximity to, or in contact with the bottom surface 504 of cartridge housing 510. Regardless of the proximity of surfaces 570 (or legs, 434, 436) and 404', as long as a notch 224 at least partially slides over or engages a tab 424, rotor assembly 555 will be inhibited from rotating within cartridge housing 510. Thus, the at least one notch 224 is configured to engage the at least one tab 424 such that rotation of the rotor assembly 555 is inhibited upon engagement. In this regard, the tab 424 and notch 224 configuration acts as a mechanical stop prohibiting inadvertent or undesired rotation of rotor assembly 555 within cartridge housing 510. This type of mechanical stop may be desired for example when, as described above, a fluid flow control device 20 comprising rotor assembly 555 is in the presence of an external magnetic field strong enough to cause alignment of the rotor assembly 555 with the external field but for the mechanical stop. If rotation of the rotor or rotor assembly is desired, i.e., deliberate adjustment is desired or required, the rotor assembly 555 is configured to lift vertically or upwardly with respect to surface 404'. When the rotor assembly 555 is lifted vertically (upward) such that a lower end 225 of the at least one notch 224 is in spaced relation and is above an upper end 425 of the at least one tab 424, the at least one notch 224 disengages the at least one tab 424 whereby the disengagement allows the rotor assembly 555 to freely rotate within cartridge housing 510.

As with cartridge assembly 400, coupling of the rotor assembly 555 with cartridge housing 510 creates cartridge assembly 500. Cartridge assembly 500, like cartridge assembly 400, is configured for use with a fluid flow control device such as fluid flow control device 20. Cartridge assembly 500 may be positioned within a fluid flow control device such that the rotor assembly 555 interacts with a valve mechanism 38 (FIG. 2) to control the flow of cerebrospinal fluid in a patient's brain. A cartridge fluid outlet 540 is therefore configured to allow passage of CSF beyond the valve mechanism 38 and out of the device 20.

With the above configurations of cartridge assemblies 400 and 500 in mind, rotation of a rotor assembly 455, 555, and thus adjustment of pressure settings of a fluid flow control device (e.g., 20) in which the cartridge assemblies 400, 500 may be placed, may be carried out deliberately via an external tool such as an adjustment tool 140, described above. Adjustment tool 140 is configured to magnetically couple to a rotor magnet or magnets (e.g., 120, 300, 315,325, 615, 317, 327 etc.) embedded in rotor assembly 455, 555 to lift the rotor assembly 455, 555 in the manner described above i.e., whereby an at least one groove 260 or notch 224 is raised above and disengaged from an at least one spline 422 or tab 424 permitting rotation of the rotor assembly 455, 555 and therefore device pressure setting adjustment via adjustment of rotor assembly 455, 555. Once the desired rotation and thus pressure setting is achieved, rotor assembly 455, 555 may be magnetically decoupled from the external tool 140 such that the at least one groove 260 or notch 224 is allowed to again or initially engage the at least one spline 422 or tab 424 and further rotation of rotor assembly 455, 555 about central rotor pivot 420 or rotor assembly 455, 555 within cartridge housing 410, 510 is prohibited until disengagement of the spline or splines 422 from the groove or grooves 260 (in the case of rotor assembly 455) or disengagement of the tab or tabs 424 from the notch or notches 224 (in the case of rotor assembly 555) is again achieved.

FIGS. 12A-12E depict a rotor assembly according to another embodiment. Rotor assembly 655 includes a housing or base 622 having a central aperture 650 for engaging a central rotor pivot or axle 620 of cartridge housing 610 (FIGS. 13A-C). Rotor assembly 655 includes a magnet 615 embedded in the base 622. Magnet 615 comprises a single magnet having a groove 616 at one end and an arrow-shaped or pointed end 617 opposite the grooved end. This configuration of magnet 615 may aid in indicating a direction of fluid flow of a valve under using imaging techniques such as x-ray or fluoroscopy. The polarization of magnet 615 is indicated by the arrow P5 which shows a horizontal polarization with respect to the lower surface 670 of rotor assembly 655. Alternatively, magnet 615 may include other magnet configurations as described herein and for example may include one or more magnets polarized in a vertical, substantially vertical or angled direction. In this embodiment, magnet 615 includes a magnet central aperture 651 aligned with the rotor central aperture 650.

Rotor assembly 655 includes a protrusion 642 projecting downwardly from lower surface 670 of assembly 655. Protrusion 642 comprises a stem portion 644 and a head portion 646. However, protrusion 642 may include a variety of configurations and shapes, where the shape or configuration of the protrusion 642 is such that it is configured to engage with or fit within or between tabs or stops 632 of cartridge housing 610 (FIG. 13A). As indicated in FIG. 12C, protrusion 642 has a lower or bottom surface 647, a length "$P_L$", a stem portion width "$P_{w1}$" and head portion width "$P_{w2}$" as well as a protrusion height, "$P_h$" (FIG. 12E). The widths, length and height may be selected to provide a protrusion 642 which is substantial enough to provide the requisite resistance to inadvertent setting changes (described further below), while being sized sufficiently small so as to minimize space taken up by the rotor assembly 655. The head 646 of protrusion 642 may include rounded corners, as shown, or may include other geometries or shapes.

As shown in FIGS. 12A-12E, protrusion 642 is positioned radially along base 622 such that protrusion 642 is substantially perpendicular to the angle of polarization P5 of magnet 615. In other words, protrusion 642 is positioned radially about the perimeter of magnet 615 such that protrusion 642 is at a ninety degree angle to P5. Positioning protrusion 642 in this manner tends to minimize forces which would pull or lift the rotor out of a locked position. For example, when rotor assembly 655 is placed within cavity 630 of cartridge housing 610, external forces acting on magnet 615 (e.g., if rotor 655 enters an MRI device at a substantially 90 degree angle to the magnetic field of the MRI equipment, as described above) may cause rotor assembly 655 to slightly rock back and forth along an axis perpendicular to P5. Since this "rocking" or tilting motion is not directly pulling up or acting on protrusion 642 (i.e. is not causing protrusion 642 to lift), despite the possible rocking or tilting motion described, the protrusion 642 tends to stay in a locked position between stops 632. Even in light of the above, protrusion 642 may alternatively be positioned along base 622 at any radial location around the perimeter of magnet 615.

FIGS. 13A-13C depict a cartridge housing in accordance with another embodiment and as described with reference to FIGS. 12A-12E above, may be particularly useful with rotor assembly 655. Several features of cartridge housing 610 may be similar to other cartridge housings described herein. For example, cartridge housing 610 includes a cartridge fluid outlet 640 a central rotor pivot or axle 620, and may include a generally similar outer housing profile. In addition, cartridge housing 610 includes a cavity 630 for receiving a rotor assembly such as 655. When rotor assembly 655 is placed within cartridge housing 610, the assembly may define a cartridge assembly (not shown) such as described with reference to cartridge assemblies 400 and 500. However, one notable difference to other cartridge housings described herein is cartridge housing 610 includes a single stair-step array 602 as opposed to a dual concentric stair-step array (e.g., 402). Since rotor assembly 655 includes only a single projection or protrusion 642, only a single stair-step array 602 is provided. As with other stair-step arrays, stair-step array 602 includes five steps (603, 604, 605, 606, 607) corresponding to five settings of a fluid flow control device (e.g., valve 20). The single-protrusion rotor assembly, single, stair-step array cartridge housing combination results in a design which may be easier to manufacture, and avoids relatively small, potentially fragile features.

As mentioned above, cartridge housing includes locks or stops 632 projecting inwardly from inner cartridge housing wall 637. Each of locks 632 include an upper surface 631 where the upper surface 631 of each lock 632 lies in the same plane (e.g., as depicted in FIG. 13B). Locks 632 are positioned radially around inner wall 637 and five locks 632 are shown which correspond to the five stair steps of array 602. Each individual lock 632 may include flattened edges 634 which angle inwardly as the lock 632 projects toward the rotor pivot 620. This flat, angled configuration allows for stem 644 of protrusion 642 to have a line to line connection with the lock 632, when the protrusion 642 is provided or located between two locks 632. Additionally, upper edges 633 of lock 632 may be chamfered to provide a smooth transition of protrusion 642 along and over lock 632 when the protrusions 642 are deliberately lifted from a first position between two locks 632 to a second position between two other locks 632 such that protrusion 642 rests on a different stair step of the array 602 in each of the two positions. For example, protrusion 642 may rest on stair step 604 in a first position and may rest on stair step 605 in a second position, and so on.

FIG. 13B is a side cross-sectional view of cartridge housing 610 taken along line A-A. A portion of stair-step array 602 can be seen as well as several of locks 632. FIG. 13C is a top view of cartridge housing 610 showing the arrangement of locks 632 around wall 637. The rotor assembly 655 is configured to be placed within a cavity (e.g., 630) of a cartridge housing, (e.g. 610). Central rotor pivot 620 is configured to engage central aperture 650 of rotor assembly 655 such that rotor assembly 655 may rotate about central rotor pivot 620 when rotor assembly 655 is positioned at various axial locations along central rotor pivot 620. However, the protrusion 642 is configured to fit between stops 632 of the housing 610 when the rotor assembly 655 is lowered into cavity 630 such that the bottom surface 647 of rotor assembly 655 is positioned lower than the upper surface 631 of stops 632. When protrusion 642 is positioned between two stops 632 in this manner, rotor assembly 655 may be in a first, locked position and will be inhibited from rotating about central rotor pivot 620. In this regard, the protrusion 642 and lock 632 interaction acts as a mechanical stop prohibiting inadvertent or undesired rotation of rotor assembly 655 about central rotor pivot 620. This type of mechanical stop may be desired for example when, as described above, a fluid flow control device 20 (or rotor, rotor assembly or magnet of a device) is in the presence of an external magnetic field strong enough to cause alignment of the rotor assembly 655 with the external field but for the mechanical stop.

Conversely, if rotation of the rotor assembly 655 is desired, i.e., deliberate adjustment is desired or required, the rotor assembly 655 is configured to lift vertically or upwardly until the lower surface 647 of protrusion 642 is located above the upper surface of locks 632. In this first, unlocked position, the rotor assembly 655 is free to rotate about the rotor pivot 620. The freedom to rotate about the rotor pivot 620, as described above, allows adjustment of the valve setting, for example, to a second, locked position (i.e., such that surface 647 or protrusion 642 rests on a step of the stair-step array 602 different from the step surface 647 rests on in a first, locked position).

Figure 15C:
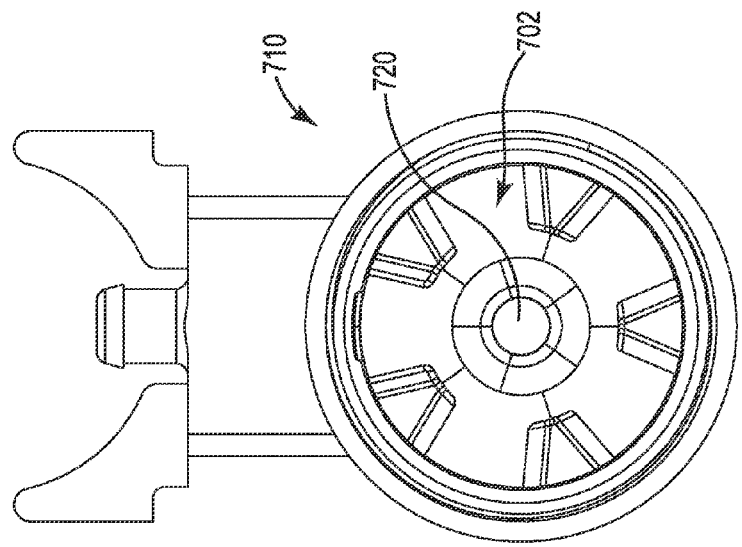
FIGS. 15A-15C depict a cartridge housing according to an embodiment.
Figure 15B:
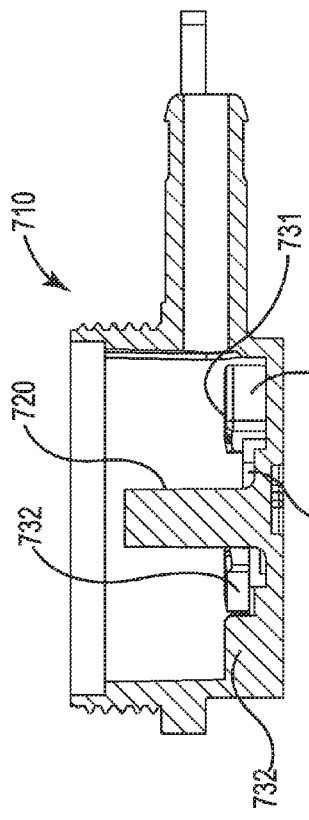
Figure 15A:
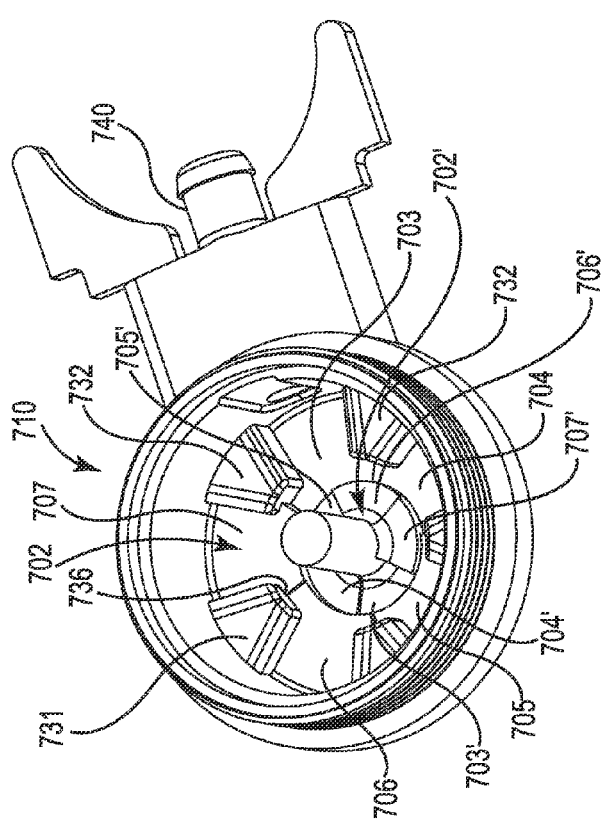

FIGS. 14A-14E and 15A-15C depict a rotor assembly and cartridge housing according to further embodiments. Rotor assembly 755 is similar to rotor assembly 655 with the exception of an additional projection, leg 752, extending from lower surface 770 of base 722. Leg 752 may comprise various shapes, configurations and sizes as long as leg 752 is sized for interaction with an inner stair-step array 702" (having steps 703', 704', 705', 706', 707') of dual-concentric stair-step array 702 (FIG. 15A). Protrusion 742 is similar to protrusion 642 described above and is likewise located perpendicular to the polarization of magnet 715. Leg 752 is located adjacent or proximate central aperture 750. Leg 752 interacts with inner stair-step array 702", such as described above with reference to feet 134, 234, 334 of FIGS. 4-9. As with the dual-concentric stair step array 102, stair-step arrays 702', 702" are constructed so that those steps opposite to one another with respect to a central rotor axis 720, subtend the same arch and are located at the same level. Thus, lower surface or edge 751 of leg 752 lies in the same plane as lower surface 747 of protrusion 742. Leg 752 interacts with inner stair-step array 702", such as described above with reference to inner legs 134, 234 etc. (FIGS. 4-9). Protrusion 742 is configured to interact with outer stair-step array 702' (having outer stair steps 703, 704, 705, 706, 707) and is configured to reside between stops 732 (FIGS. 15A-C) similar to protrusion 642 and stops 632 such that when lower surface 747 of protrusion 742 is lower than an upper surface 731 of stops 732, rotation of rotor assembly 755 about central rotor pivot or axle 720 is essentially prohibited while raising rotor assembly 755 such that the lower surface 747 is above upper surface 731 allows rotor assembly 755 to rotate about axle 720 so as to adjust the setting as described above.

FIGS. 16A-14E and 17A-15C depict a rotor assembly and cartridge housing according to further embodiments. Rotor assembly 855 is similar to rotor assemblies 655 and 755. Rotor assembly is similar to rotor assembly 655 in that two projections 844 and 846, if coupled together, may resemble single projection 642 (FIG. 12B). Rotor assembly is similar to rotor assembly 755 in that the assembly includes two protrusion or projections, a tab 846, and a stem 844, extending from lower surface 870 of base 822. Tab 846 may comprise various shapes, configurations and sizes as long as tab 852 is sized for interaction with an inner stair-step array 802" (having steps 803', 804', 805', 806', 807') of dual-concentric stair-step array 802 (FIG. 17A). A difference to rotor assembly 755 is tab 846 is spaced radially from (rather than adjacent to) central aperture 850. Tab 846 interacts with inner stair-step array 802", such as described above with reference to feet 134, 234, 334 and leg 752 of FIGS. 4-9, 14B.

Stem 844 is similar to protrusions or projections 642 and 742 described above in that stem 844 is likewise located perpendicular to the polarization of magnet 815. Stem 844 is configured to interact with outer stair-step array 802' (having outer stair steps 803, 804, 805, 806, 807) and is configured to reside between stops 832 (FIGS. 17A-C) similar to projections 642, 742 and stops 632, 732. Lower surface or edge 848 of tab 846 lies in the same plane as lower surface 847 of stem 844. Stair step array 802 is similar to array 702 although inner array 802' may be radially wider than inner array 702'. Thus, when lower surface 847 of stem 844 is lower than an upper surface 831 of stops 832 of cartridge housing 810, rotation of rotor assembly 855 about central rotor pivot or axle 820 is essentially prohibited, while raising rotor assembly 855 such that the lower surface 847 is above upper surface 831 allows rotor assembly 855 to rotate about axle 820 so as to adjust the setting as described above.

The various rotor assemblies and cartridge housings described herein may comprise a variety of suitable materials such as suitable polymers. For example, rotor assemblies may comprise polysulfone and cartridge housings may comprise polysulfone, acetal, PEEK, polyphelylene, polyphenylsulfone, polyether sulfone, as but several non-limiting examples. Any suitable material may be used and may for example, include any material having a tensile strength high enough to prevent fracture of a central rotor pivot or axle (referenced generally).

FIG. 18 shows two magnets 350, 360 useful with a rotor assembly e.g., 100, 200, 455, 555. The magnets 350 and 360 depict conventional horizontal polarization indicated at arrows P3 and P4. That is, each magnet 350, 360 is magnetized in a plane horizontal to an upper planar surface 351, 361 of the magnet. Stated another way, magnets are magnetized in a direction substantially perpendicular to a central horizontal magnet axis A1 or A2. FIG. 19 depicts two magnets 317 and 327 according to an embodiment. Magnets 317 and 327 comprise horizontal upper planar surfaces 520 and 521 which may be substantially flat. Magnets 317 and 327 also comprise horizontal magnet axes H1 and H2, respectively. In contrast to the horizontal polarity P3, P4 of conventional magnets 350 and 360, magnets 317 and 327 comprise angled magnetization indicated at arrows P1' and P2', where the angle of polarization with respect to the horizontal magnet axes H1 or H2 may be any angle greater than 0 and less than 90 degrees. For example, the angle of polarization may be approximately greater than 0 and less than or equal to 20 degrees relative to horizontal magnet axes H1 or H2.

In the embodiment of magnet 327 shown, an angle of magnetization of 15 degrees is depicted. It is to be understood, however, that magnets 317, 327 may comprise any angle of magnetization. Magnets 315 and 325 may be used in any of the rotor assemblies (e.g., 10, 200, 455, 555) described herein above or any other rotor assembly or fluid flow control device (e.g., 20). Magnets 317 and 327 may be positioned or embedded in a rotor assembly 100, 200, 455, 555, cartridge housing 410, 510 or fluid flow control device 20 such that horizontal planar surfaces 520, 521 lie in a plane substantially perpendicular to a central vertical rotor axis or central vertical pivot axis A, A' or A" (FIGS. 2, 7 and 10) of a rotor assembly 100, 200, 455 or cartridge housing 410, 510 while magnetization or polarization of magnets 315, 325 remains at an angle 'with respect to the horizontal magnet axes A, A' or A". In other words, magnets 315, 327 themselves are not substantially or significantly tilted with respect to a base (e.g., 122, 222, 522) or cartridge housing (e.g., 41, 410, 510), rather, the magnetization or polarization of magnets 315, 325 is "tilted" or angled by virtue of processing and/or manufacturing methods used in producing the magnets 317, 327 which will be further described below. FIG. 20 describes an alternative embodiment where magnets 317 and 327 are similar to magnets 315 and 327 with the exception that the magnets are joined or coupled together and may thus form a single magnet.

Figure 21:
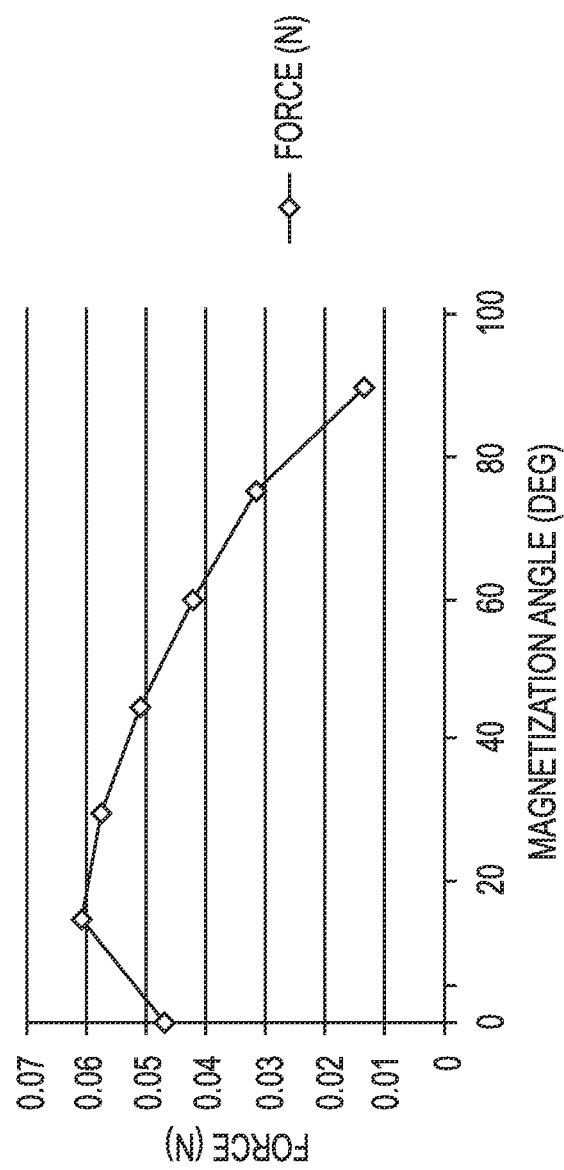
FIG. 21 is a plot illustrating attraction force between a fluid flow control device accessory tool and a rotor assembly of a fluid flow control device for rotor magnets magnetized at various magnetization angles according to the disclosure.

Tilting or angling the magnetization or polarization P1', P2' of magnets 317, 327 may allow for or result in stronger magnetic forces between an external device tool 140 and a rotor magnet or magnets e.g., 300, 315,310, 325 etc. when deliberate adjustment, location or indication of a pressure setting of a fluid flow control device, or shunt valve is desired. Tissues located between the site of implant of a fluid flow control device 20 and the area external to the patient in proximity to the implanted device may interfere with magnetic coupling or adequate coupling between a tool 140 and rotor assembly 100, 200, 455. It has been found that angling the magnetization or polarization P1', P2' may advantageously produce higher magnetic forces between an external tool 140 and rotor magnets e.g., 317, 327, may provide better resistance to demagnetization, and when used with an axle or rotor pivot such as central rotor pivot 420 (FIG. 9A), may create additional friction in an MRI environment which may aid in resisting alignment with the MRI field. The higher forces between an external tool and rotor magnets is illustrated in the graph of FIG. 21. FIG. 21 is a computer simulated plot of Force (in Newtons) versus a Magnetization angle (in degrees) from a horizontal magnet axis such as described above with reference to FIG. 19. As illustrated in the plot, Force may be greatest where magnets comprise a magnetization angle between approximately 0 and 20 degrees.

In order to produce or manufacture magnets with angled polarization as disclosed above, the magnets 315, 317, 325, 327 may be machined at an angle. Magnets in general and some magnets useful with fluid flow control devices are typically or conventionally machined with the grain of the magnetic material parallel to the magnet dimensions, such as illustrated by magnets 350 and 360 described above. If instead, and according to the disclosure, magnetic material is machined so that the grain of the material matches the desired polarization angle e.g., P1', P2', then the magnet or magnets (e.g., 317, 327) may be positioned in a rotor assembly (e.g., 200, 455, 555) in a substantially physically flat (or horizontal as described above) configuration while maintaining angled polarity P1', P2' with the advantage of increased coupling strength, as described above, and a space saving design.

Although the present disclosure has been described with reference to preferred embodiments, workers skilled in the art will recognize that changes can be made in form and detail without departing from the spirit and scope of the present disclosure.

What is claimed is:

1. An implantable fluid flow control device comprising:
    an inlet;
    an outlet spaced from the inlet;
    a valve mechanism for controlling a flow of fluid from the inlet to the outlet;
    a cartridge housing comprising a stair-step array and a plurality of stops each projecting from an inner wall of the cartridge housing between an end of each step of the stair-step array;
    a rotor assembly comprising a magnet mounted in a base and a protrusion projecting from a lower surface of the base;
    wherein the rotor assembly is configured for placement at least partially within the cartridge housing and the protrusion is configured to reside between two stops of the plurality of stops such that the rotor assembly is in a first, locked position in the cartridge housing.

2. The implantable fluid flow control device of claim 1, wherein the rotor assembly is configured to magnetically couple to an adjustment tool whereby the rotor assembly is configured to lift upwardly with respect to the stair-step array and the plurality of stops upon magnetically coupling with the adjustment tool.

3. The implantable fluid flow control device of claim 1, wherein the protrusion is spaced along radially about the base such that the protrusion is substantially perpendicular to a polarity of the magnet.

* * * * *